US012612906B2

(12) United States Patent
Löffler et al.

(10) Patent No.: US 12,612,906 B2
(45) Date of Patent: Apr. 28, 2026

(54) ROLLER PUMP FOR USE WITH A PERFUSION SYSTEM AND ASSOCIATED METHODS

(71) Applicant: LivaNova Deutschland GmbH, Munich (DE)

(72) Inventors: Philipp Löffler, Freising (DE); Matthias Zeppenfeld, Munich (DE)

(73) Assignee: LivaNova Deutschland GmbH, Munich (DE)

( * ) Notice: Subject to any disclaimer, the term of this patent is extended or adjusted under 35 U.S.C. 154(b) by 0 days.

(21) Appl. No.: 18/923,024

(22) Filed: Oct. 22, 2024

(65) Prior Publication Data

US 2026/0110295 A1     Apr. 23, 2026

(51) Int. Cl.
| | |
|---|---|
| *F04B 43/12* | (2006.01) |
| *A61M 1/36* | (2006.01) |
| *A61M 5/142* | (2006.01) |
| *A61M 60/109* | (2021.01) |
| *A61M 60/279* | (2021.01) |
| *A61M 60/441* | (2021.01) |

(52) U.S. Cl.
CPC ....... *F04B 43/1276* (2013.01); *A61M 1/3666* (2013.01); *A61M 5/14232* (2013.01);
(Continued)

(58) Field of Classification Search
CPC .. F04B 43/1253; F04B 43/1276; F04B 49/06; F04B 49/065; A61M 1/3666;
(Continued)

(56) References Cited

U.S. PATENT DOCUMENTS

| | | | | |
|---|---|---|---|---|
| 4,278,085 A | * | 7/1981 | Shim ................. | A61M 5/14232 |
| | | | | 604/153 |
| 4,547,136 A | | 10/1985 | Rothstein | |

(Continued)

FOREIGN PATENT DOCUMENTS

DE          3326785 A1     2/1985

OTHER PUBLICATIONS

Extended European Search Report and Search Opinion received for EP Application No. 25203015.0, mailed on Nov. 6, 2025, 12 pages.
(Continued)

*Primary Examiner* — Loren C Edwards
(74) *Attorney, Agent, or Firm* — Seager, Tufte & Wickhem LLP

(57) ABSTRACT

A roller pump includes a roller pump rotor including a first roller arm having a first roller rotatably coupled thereto and a second roller arm having a second roller rotatably coupled thereto, a raceway disposed around the rotor, a pump motor configured to rotate the rotor relative to the raceway, and an electronic actuator disposed on the rotor, wherein the actuator is configured to change a radial position of the first and second rollers. The actuator may be couplable to the motor such that the motor is capable of rotating the rotor and changing the radial position of the first and second rollers. An extracorporeal perfusion system includes a fluid reservoir, an oxygenator, flexible tubing coupling the reservoir to the oxygenator, and the roller pump, wherein the flexible tubing is disposed within the raceway. The motor is configured to rotate the rotor to cause fluid to flow within the tubing.

19 Claims, 10 Drawing Sheets

(52) U.S. Cl.
CPC ........ *A61M 60/109* (2021.01); *A61M 60/279* (2021.01); *A61M 60/441* (2021.01)

(58) Field of Classification Search
CPC ............ A61M 5/14232; A61M 60/109; A61M 60/279; A61M 60/424; A61M 60/438; A61M 60/441
See application file for complete search history.

(56) References Cited

U.S. PATENT DOCUMENTS

| | | | |
|---|---|---|---|
| 5,215,450 A * | 6/1993 | Tamari | F04B 43/0072 |
| | | | 138/119 |
| 5,586,872 A | 12/1996 | Skobelev et al. | |
| 5,657,000 A | 8/1997 | Ellingboe | |
| 8,197,236 B2 | 6/2012 | McIntosh | |
| 9,422,932 B2 | 8/2016 | Petersen et al. | |
| 10,012,226 B2 | 7/2018 | Petersen et al. | |
| 2014/0127063 A1 * | 5/2014 | Petersen | F04B 49/065 |
| | | | 417/476 |
| 2019/0047295 A1 | 2/2019 | Yokoi | |
| 2021/0206521 A1 | 7/2021 | Cichy et al. | |
| 2021/0254614 A1 | 8/2021 | Michel | |

OTHER PUBLICATIONS

Extended European Search Report and Search Opinion received for EP Application No. 25203016, mailed on Nov. 10, 2025, 10 pages.

* cited by examiner

ROLLER PUMP FOR USE WITH A PERFUSION SYSTEM AND ASSOCIATED METHODS

TECHNICAL FIELD

The present disclosure relates to a roller pump for use with an extracorporeal perfusion system and/or methods for manufacturing and/or using the roller pump. More particularly, the present disclosure relates to a roller pump having a mechatronic occlusion mechanism and/or methods of use.

BACKGROUND

Some medical procedures (e.g., medical procedures which treat cardiac or respiratory disease) may require the use of a life support system that supports cardiac and pulmonary functions by artificially supporting the heart and the lung function. In some instances, this may be carried out by an extracorporeal perfusion system. An extracorporeal perfusion system may provide both cardiac and respiratory support to a patient whose heart and lungs are unable to provide an adequate amount of gas exchange during a cardiac and pulmonary procedure. Extracorporeal perfusion works by removing blood from a patient's body to oxygenate the red blood cells while also removing carbon dioxide. The oxygenated blood is then returned to the patient.

Extracorporeal perfusion systems may include multiple devices that together form a blood recirculation loop between the patient and a blood oxygenator. For example, some extracorporeal perfusion systems may include a blood reservoir, a blood pump (such as a roller pump) to power blood flow, an oxygenator to oxygenate the blood, a device to filter the blood (which may be included within the oxygenator and/or the reservoir in some systems), one or more sensors positioned at various locations along fluid pathways and one or more control units. It can be appreciated that a fluid pathway (e.g., tubing) may extend from the patient to the blood reservoir, then towards a blood pump, then pass through the oxygenator and close the loop by returning to the patient. Accordingly, the blood pump may assist the heart by pumping blood through the circulation loop, while the oxygenator may assist the lungs by oxygenating blood that is eventually returned to the patient.

Roller pumps used in extracorporeal perfusion systems typically require shutting down the roller pump in order to adjust the flow rate by changing the degree of occlusion of a tubing positioned within the roller pump, etc. Such adjustments are made manually and are time consuming. There is an ongoing need for alternative devices, components, configurations, and/or methods of use and/or manufacture of said devices and/or components to improve usability.

SUMMARY

In one example, a roller pump may comprise a roller pump rotor comprising a first roller arm having a first roller rotatably coupled thereto and a second roller arm having a second roller rotatably coupled thereto, a raceway disposed around the roller pump rotor and configured to receive a flexible tubing, a pump motor configured to rotate the roller pump rotor relative to the raceway, and an electronic actuator disposed on the roller pump rotor, wherein the electronic actuator is configured to change a radial position of the first roller and the second roller relative to a central axis of the roller pump rotor.

In addition, or alternatively, to any example described herein, the radial position of the first roller and the second roller corresponds to a degree of occlusion of the flexible tubing.

In addition, or alternatively, to any example described herein, as the radial position of the first roller and the second roller moves away from the central axis of the roller pump rotor, the degree of occlusion of the flexible tubing increases.

In addition, or alternatively, to any example described herein, as the radial position of the first roller and the second roller moves toward the central axis of the roller pump rotor, the degree of occlusion of the flexible tubing decreases.

In addition, or alternatively, to any example described herein, the electronic actuator functions independently of the pump motor to change the radial position of the first roller and the second roller relative to the central axis of the roller pump rotor.

In addition, or alternatively, to any example described herein, the electronic actuator is configured to change the radial position of the first roller and the second roller relative to the central axis of the roller pump rotor while the pump motor is rotating the roller pump rotor relative to the raceway.

In addition, or alternatively, to any example described herein, the roller pump may comprise a threaded mechanism configured to engage the first roller arm and the second roller arm such that actuation of the threaded mechanism by the electronic actuator changes the radial position of the first roller and the second roller relative to the central axis of the roller pump rotor.

In addition, or alternatively, to any example described herein, the threaded mechanism comprises a threaded rod and a scissors assembly.

In addition, or alternatively, to any example described herein, the threaded mechanism may comprise a flattened disk having a center and a peripheral edge, and a spiral thread extending between the center and the peripheral edge.

In addition, or alternatively, to any example described herein, the first roller arm comprises threads configured to engage with the spiral thread of the threaded mechanism and the second roller arm comprises threads configured to engage with the spiral thread of the threaded mechanism.

In addition, or alternatively, to any example described herein, the electronic actuator comprises a wedge configured to move perpendicularly to the first roller arm and the second roller arm to change the radial position of the first roller and the second roller relative to the central axis of the roller pump rotor.

In addition, or alternatively, to any example described herein, the electronic actuator comprises a rack and pinion system configured to change the radial position of the first roller and the second roller relative to the central axis of the roller pump rotor.

In addition, or alternatively, to any example described herein, a portion of the first roller arm overlaps a portion of the second roller arm.

In addition, or alternatively, to any example described herein, the first roller arm is pivotably coupled to the roller pump rotor at a first location and the second roller arm is pivotably coupled to the roller pump rotor at a second location spaced part from the first location. The electronic actuator may comprise a gear disposed coaxial with the central axis of the roller pump rotor and the gear is configured to engage the first roller arm and the second roller arm to change the radial position of the first roller and the second roller relative to the central axis of the roller pump rotor.

In addition, or alternatively, to any example described herein, the raceway comprises a force sensor configured to sense force exerted against the flexible tubing by the first roller and the second roller.

In addition, or alternatively, to any example described herein, the electronic actuator is configured to automatically change the radial position of the first roller and the second roller relative to the roller pump rotor in order to maintain a desired flow rate through the flexible tubing.

In addition, or alternatively, to any example described herein, the electronic actuator is configured to automatically change the radial position of the first roller and the second roller relative to the roller pump rotor in response to pressure or flow rate of fluid within the flexible tubing.

In addition, or alternatively, to any example described herein, and in a second example, a roller pump may comprise a roller pump rotor comprising a first roller arm having a first roller rotatably coupled thereto and a second roller arm having a second roller rotatably coupled thereto, a raceway disposed around the roller pump rotor and configured to receive a flexible tubing, a pump motor configured to rotate the roller pump rotor relative to the raceway, and an electronic actuator disposed on the roller pump rotor, wherein the electronic actuator is configured to change a radial position of the first roller and the second roller relative to a central axis of the roller pump rotor. The electronic actuator may be couplable to the pump motor such that the pump motor is capable of rotating the roller pump rotor and changing the radial position of the first roller and the second roller relative to the roller pump rotor.

In addition, or alternatively, to any example described herein, the electronic actuator comprises a clutch mechanism configured to selectively couple the pump motor with the first roller arm and the second roller arm.

In addition, or alternatively, to any example described herein, and in a third example, an extracorporeal perfusion system may comprise a fluid reservoir, an oxygenator, flexible tubing fluidly coupling the fluid reservoir to the oxygenator, and a roller pump comprising a roller pump rotor comprising a first roller arm having a first roller rotatably coupled thereto and a second roller arm having a second roller rotatably coupled thereto, a raceway disposed around the roller pump rotor and configured to receive a flexible tubing, a pump motor configured to rotate the roller pump rotor relative to the raceway, and an electronic actuator disposed on the roller pump rotor, wherein the electronic actuator is configured to change a radial position of the first roller and the second roller relative to a central axis of the roller pump rotor. The flexible tubing may be disposed within the raceway and the first roller and the second roller are engaged with the flexible tubing. The pump motor may be configured to rotate the roller pump rotor relative to the raceway to cause fluid to flow within the flexible tubing from the fluid reservoir to the oxygenator.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
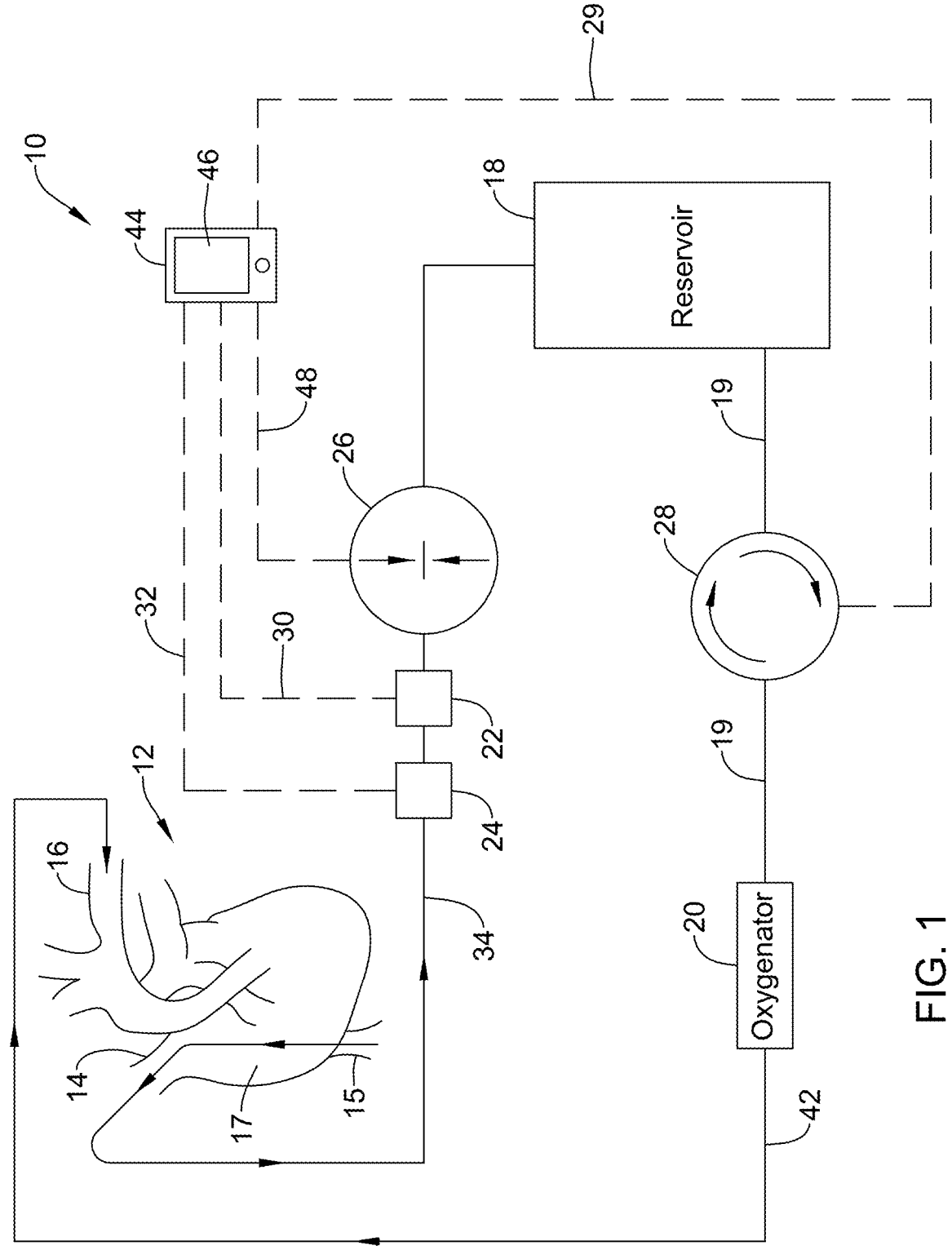
FIG. 1 schematically illustrates selected aspects of an extracorporeal perfusion system.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the disclosure. The detailed description and drawings are intended to illustrate example embodiments of the disclosure but not limit the disclosure. Those skilled in the art will recognize that the various elements described and/or shown may be arranged in various combinations and configurations without departing from the scope of the disclosure.

For the following defined terms, these definitions shall be applied, unless a different definition is given in the claims or elsewhere in this specification.

As used herein in association with values (e.g., terms of magnitude, measurement, and/or other degrees of qualitative and/or quantitative observations that are used herein with respect to characteristics (e.g., dimensions, measurements, attributes, components, etc.) and/or ranges thereof, of tangible things (e.g., products, inventory, etc.) and/or intangible things (e.g., data, information, etc.), portions of things (e.g., percentages, fractions), calculations, data models, dynamic system models, algorithms, parameters, etc.), "about" and "approximately" may be used, interchangeably, to refer to a value, configuration, orientation, and/or other characteristic that is equal to (or the same as) the stated value, configuration, orientation, and/or other characteristic, or equal to (or the same as) a value, configuration, orientation, and/or other characteristic that is reasonably close to the stated value, configuration, orientation, and/or other characteristic, but that may differ by a reasonably small amount such as will be understood and readily ascertained by individuals having ordinary skill in the relevant arts to be attributable to one or more of the following: measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

The recitation of numerical ranges by endpoints includes all numbers within that range (e.g., 1 to 5 includes 1, 1.5, 2, 2.75, 3, 3.80, 4, and 5). All numeric values are herein assumed to be modified by the term "about", whether or not explicitly indicated. In some instances, the term "about" may include numbers that are rounded to the nearest significant figure.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to implement the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Additionally, it should be noted that in any given figure, some features may not be shown, or may be shown schematically, for clarity and/or simplicity. Additional details regarding some components and/or method steps may be illustrated in other figures in greater detail. It is noted that some reference numbers may be discussed but are not expressly shown with respect to a particular figure. Reference numbers discussed but not expressly shown may be shown in other figures. Similarly, some reference numbers shown but not expressly discussed may be discussed with respect to other figures herein. The systems, devices, and/or methods disclosed herein may provide a number of desirable features and benefits as described in more detail below.

In a normal heart, blood circulates via a closed path whereby deoxygenated (venous) blood enters the right atrium via both the superior vena cava and inferior vena cava. The venous blood then passes through the right ventricle and is pumped via the pulmonary artery to the lungs, where it absorbs oxygen and releases carbon dioxide. After absorbing oxygen and releasing carbon dioxide in the lungs, the blood becomes oxygenated arterial blood. The oxygenated blood is then returned via the pulmonary veins to the left atrium and is passed to the left ventricle. The oxygenated arterial blood is then pumped through the aorta and eventually throughout the body.

It can be appreciated that if the lungs are incapable of sufficiently oxygenating blood and/or removing carbon dioxide, an oxygenator located outside the body may be used to oxygenate the blood and/or remove carbon dioxide. As discussed above, an extracorporeal perfusion system may be utilized to support patients while medical treatments (e.g., heart surgery) are performed to treat an underlying illness. When supported via extracorporeal perfusion, oxygenation of the patient's blood and removal of carbon dioxide may occur outside the body.

Extracorporeal perfusion is generally performed using an extracorporeal perfusion system (such as a heart-lung bypass system), wherein the system may be referred to as a "circuit." The circuit may include at least one fluid pathway exterior of the patient, such as one or more tubing pathways designed to transfer blood from a patient's body to the oxygenator and back into the patient. As described above, the oxygenator may add oxygen to the blood while also removing carbon dioxide (e.g., the oxygenator performs the function of a healthy lung).

In some examples, an extracorporeal perfusion system may include a blood pump, oxygenator, tubing pathways (for transfer to and from the body), sensors (e.g., flow, pressure, bubble, temperature, oxygen, carbon dioxide, etc.), a heat exchanger (to cool and/or heat the blood), a control unit, and arterial and/or venous access points for the collection of blood in the circuit. It can be appreciated that the function of the blood pump is to generate blood flow within the extracorporeal perfusion system (e.g., circulate blood from the patient to the oxygenator and back to the patient) and to also generate blood pressure within the patient's vascular system. The blood pump may be positioned in the tubing pathway between the patient and the oxygenator. In some extracorporeal perfusion systems, the blood pump may comprise a roller pump utilized to generate blood flow within the extracorporeal perfusion system. However, in other extracorporeal perfusion systems, other types of blood pumps (e.g., centrifugal pumps, etc.) may be utilized to generate blood flow within the extracorporeal perfusion system.

In some extracorporeal perfusion systems, the oxygenator may include a housing having multiple chambers or pathways separated by a semi-permeable membrane, whereby the patient's blood may flow through one chamber or pathway, while an oxygen gas mixture (i.e., sweep gas) flows through another chamber or pathway. The semi-permeable membrane may include multiple microporous hollow fibers, each fiber having a lumen extending therethrough through which the oxygen gas mixture flows. The gas exchange may occur via diffusion of the gases across multiple microporous fibers, whereby oxygen moves from the inside of the hollow fibers into the blood while carbon dioxide diffuses from the blood into the interior of the hollow fibers, where it is swept away by the sweep gas flowing through the fiber. This gas exchange allows for oxygenation of venous blood and removal of carbon dioxide. In some extracorporeal perfusion systems, the oxygenator may include integrated heat exchangers that allow circulating blood to be cooled and/or warmed prior to returning to the patient.

In some instances, it may be desirable to control one or more parameters of blood flow through the various fluid pathways of the extracorporeal perfusion system. For example, it may be desirable to control the flowrate of blood within one or more fluid pathways within the extracorporeal perfusion system. In some examples, the flowrate of blood within the fluid pathways of the extracorporeal perfusion system may be controlled via a combination of clamps, sensors, and pumps, one or more of which may be coupled to the various fluid pathways of the extracorporeal perfusion system. In some examples, one or more of the clamps, sensors and pumps may be in communication (e.g., wireless, wired communication, or other communication means capable of transmitting signals) with a control unit, whereby the control unit may be configured to operate one or more of the clamps, sensors and pumps in various combinations to control the flow of blood within the fluid pathways of the extracorporeal perfusion system.

FIG. 1 schematically illustrates an extracorporeal perfusion system 10 coupled to a patient's heart 12. In some embodiments, the extracorporeal perfusion system 10 may comprise a fluid reservoir 18 and an oxygenator 20. In some embodiments, the extracorporeal perfusion system 10 may comprise flexible tubing 19 fluidly coupling the fluid reservoir 18 to the oxygenator 20. In some embodiments, the extracorporeal perfusion system 10 may comprise a clamp 26, a flow sensor 22, and/or a pressure sensor 24. In some embodiments, the extracorporeal perfusion system 10 may comprise a roller pump 28 disposed along the flexible tubing 19. In some embodiments, the roller pump 28 may be disposed elsewhere within the extracorporeal perfusion system 10. In some embodiments, the extracorporeal perfusion system 10 may comprise a control unit 44. In some embodiments, the pressure sensor 24 may be positioned adjacent to or integrated with the fluid reservoir 18. Additionally, the extracorporeal perfusion system 10 may comprise one or more fluid pathways (e.g., refs 34, 42) extending between various components of the extracorporeal perfusion system 10.

In some embodiments, the fluid reservoir 18 of the extracorporeal perfusion system 10 may be designed to hold fluid (e.g., blood, priming fluid, etc.) which may be gravity fed from a patient, such as the patient's superior vena cava (SVC) 14 and inferior vena cava (IVC) 15 or, alternatively, from a first cannula placed in the patient's right atrium 17 through a venous fluid pathway 34 to the fluid reservoir 18. Fluid (e.g., blood, priming fluid, etc.) from the fluid reservoir 18 may then pass to the roller pump 28 within the flexible tubing 19 and/or along an arterial fluid pathway 42. The roller pump 28 may then pump the fluid (e.g., blood, priming fluid, etc.) into the oxygenator 20 within the flexible tubing 19 and/or along the arterial fluid pathway 42. After gas exchange takes place within the oxygenator 20, the oxygenated fluid (e.g., blood, priming fluid, etc.) may return to the patient's vascular system, such as via a second cannula placed in the aorta 16.

In some examples, the fluid reservoir 18 and the oxygenator 20 may be coupled together in a variety of configurations. In one example, the fluid reservoir 18 and the oxygenator 20 may be separate components within the extracorporeal perfusion system 10 fluidly coupled together via the flexible tubing 19, as shown in FIG. 1. In some alternative examples, the oxygenator 20 and the fluid reservoir 18 may be combined into a single unit.

In some embodiments, the extracorporeal perfusion system 10 may comprise the clamp 26, the flow sensor 22, and/or the pressure sensor 24 positioned along various fluid pathways (e.g., the venous fluid pathway 34 and/or the arterial fluid pathway 42), whereby the clamp 26, the flow sensor 22, and/or the pressure sensor 24 may help regulate the flow of fluid (e.g., blood, priming fluid, etc.) through the various fluid pathways. For example, FIG. 1 illustrates that the extracorporeal perfusion system 10 includes the clamp 26, the flow sensor 22, and the pressure sensor 24 positioned along the venous fluid pathway 34 and/or upstream of the fluid reservoir 18, and the extracorporeal perfusion system 10 is described herein in this context. However, it shall be recognized that in some embodiments, the clamp 26, the flow sensor 22, and/or the pressure sensor 24 may be positioned along the arterial fluid pathway 42 and/or elsewhere within the extracorporeal perfusion system 10, and various discussion and/or description provided herein may be applied in a similar manner. In some embodiments, the clamp 26, the flow sensor 22, and/or the pressure sensor 24 may be positioned along both the venous fluid pathway 34 and the arterial fluid pathway 42, or in various combinations along the venous fluid pathway 34 and the arterial fluid pathway 42.

In some embodiments, the venous fluid pathway 34 and/or the arterial fluid pathway 42 may be defined by and/or formed from a tubing having a wall and a lumen extending therein. The lumen of the tubing may have a cross-sectional area which, along with the velocity of the fluid (e.g., blood, priming fluid, etc.) flowing through the tubing, defines the volume of fluid (e.g., blood, priming fluid, etc.) which may pass through the tubing over a given time period. In some embodiments, the tubing used to define the venous fluid pathway 34 and/or the arterial fluid pathway 42 may be formed from a polymer material (e.g., polyvinyl, etc.). For example, the tubing used to define the venous fluid pathway 34 and/or the arterial fluid pathway 42 may be constructed from polyvinyl chloride (PVC) because it is flexible, compatible with blood, inert, nontoxic, smooth, tough, transparent, resistant to kinking and collapse, and may be heat sterilized. In some embodiments, the venous fluid pathway 34 and/or the arterial fluid pathway 42 may comprise and/or be formed from silicone. In some embodiments, the venous fluid pathway 34 and/or the arterial fluid pathway 42, or portions thereof, may be formed from rigid tubing components having a lumen extending therethrough. Other configurations and/or materials are also contemplated.

In some embodiments, the clamp 26 may be disposed external to the venous fluid pathway 34 and/or the arterial fluid pathway 42 (e.g., the tubing) and/or may be devoid of fluid communication with the fluid (e.g., blood, priming fluid, etc.) flowing within the venous fluid pathway 34 and/or the arterial fluid pathway 42 (e.g., the tubing) to avoid contamination of the fluid (e.g., blood, priming fluid, etc.). In some embodiments, when positioned along the venous fluid pathway 34 and/or the arterial fluid pathway 42, the clamp 26 may be configured to actuate such that the clamp 26 decreases or increases the cross-sectional area of a lumen of a component defining the venous fluid pathway 34 and/or the arterial fluid pathway 42 (e.g., the tubing). In some embodiments, the clamp 26 may engage tubing defining the venous fluid pathway 34 and/or the arterial fluid pathway 42. In these examples, the tubing defining the venous fluid pathway 34 and/or the arterial fluid pathway 42 may extend within at least a portion of the clamp 26, whereby actuation of the clamp 26 may either clamp down and restrict the cross-sectional area of the tubing or may release and expand the cross-sectional area of the tubing defining the venous fluid pathway 34 and/or the arterial fluid pathway 42. In other words, the clamp 26 may be designed to physically deform the tubing to adjust the cross-sectional area of the lumen (which may, in turn, increase the resistance of the tubing), and therefore, the flow rate of fluid (e.g., blood, priming fluid, etc.) through the tubing.

In some embodiments, the clamp 26 may be in fluid communication with the venous fluid pathway 34 and/or the arterial fluid pathway 42 and/or fluid (e.g., blood, priming fluid, etc.) disposed and/or flowing therein. In some embodiments, the clamp 26 may comprise a component (e.g., a ball valve, iris, etc.) having an adjustable lumen size and/or restriction designed to adjust the flow rate of fluid (e.g., blood, priming fluid, etc.) through the clamp 26. The clamp 26 may be designed such that a first section of tubing (e.g., flexible, semi-rigid, rigid tubing) may be inserted into an inlet of the clamp 26 and a second section of tubing may be inserted into an outlet of the clamp 26. Accordingly, the fluid (e.g., blood, priming fluid, etc.) may flow through the first section of tubing into the clamp 26, through a valve located in the clamp 26, and exit the clamp 26 via an outlet of the clamp 26 and into the second section of tubing. Other configurations are also contemplated.

In some embodiments, the flow sensor 22 may be fixedly attached to the clamp 26 (e.g., the flow sensor 22 may be an integrated component of the clamp 26). However, in other examples, the flow sensor 22 may be a separate and distinct component, separated from the clamp 26 and positioned along any portion of the venous fluid pathway 34 and/or the arterial fluid pathway 42. In some examples, the flow sensor 22 may be positioned on an inner surface, the outer surface or within a wall of the tubing defining the venous fluid pathway 34 and/or the arterial fluid pathway 42. In other examples, the flow sensor 22 may be positioned adjacent to a component (e.g., tubing) defining the venous fluid pathway 34 and/or the arterial fluid pathway 42. The flow sensor 22 may be a flow sensor configured to sense (e.g., detect, measure, compute, monitor, etc.) the flow rate of fluid (e.g., blood, priming fluid, etc.) passing through the extracorporeal perfusion system 10, the venous fluid pathway 34, and/or the arterial fluid pathway 42.

In some embodiments, the pressure sensor 24 may be positioned along the venous fluid pathway 34 and/or the arterial fluid pathway 42. In some embodiments, the pressure sensor 24 may be fixedly attached to the clamp 26 (e.g., the pressure sensor 24 may be an integrated component of the clamp 26). In some embodiments, the pressure sensor 24 may be a separate and distinct component, separated from the clamp 26 and positioned along any portion of the venous fluid pathway 34 and/or the arterial fluid pathway 42. In some embodiments, the pressure sensor 24 may be positioned on an inner surface, the outer surface or within a wall of the tubing defining the venous fluid pathway 34 and/or the arterial fluid pathway 42. In some embodiments, the pressure sensor 24 may be positioned adjacent to a component (e.g., tubing) defining the venous fluid pathway 34 and/or the arterial fluid pathway 42. The pressure sensor 24 may be a pressure sensor configured to sense (e.g., detect, measure, compute, monitor, etc.) the pressure of fluid (e.g., blood, priming fluid, etc.) passing through the extracorporeal perfusion system 10, the venous fluid pathway 34, and/or the arterial fluid pathway 42. In some embodiments the pressure sensor 24 may be in fluid communication with the venous fluid pathway 34, the arterial fluid pathway 42, and/or the flexible tubing 19.

In some embodiments, the pressure sensor 24 may be positioned within and/or may be integrated with the fluid reservoir 18. In some embodiments, the pressure sensor 24 may be disposed adjacent to and/or may be positioned at the roller pump 28. In some embodiments, the pressure sensor 24 may be fixedly attached to and/or may be an integrated component of the roller pump 28. Other configurations are also contemplated.

In some embodiments, the extracorporeal perfusion system 10 may include additional sensors positioned along the venous fluid pathway 34 and/or the arterial fluid pathway 42. In some embodiments, the extracorporeal perfusion system 10 may include one or more sensors for monitoring temperatures, bubbles, oxygen saturation, carbon dioxide content, blood gases, or other fluid (e.g., blood, priming fluid, etc.) parameters. In some embodiments, a single sensor may be configured to sense multiple fluid (e.g., blood, priming fluid, etc.) parameters including flow rate, pressures, temperatures, bubbles, oxygen saturation, carbon dioxide content, blood gases, etc.

As discussed herein, the extracorporeal perfusion system 10 may comprise a control unit 44. In some embodiments, the control unit 44 may include a visual display 46 and/or one or more control devices (e.g., knobs, buttons, switches, etc.). In some embodiments, the visual display 46 may be separate and/or spaced apart from the control unit 44. In some embodiments, the visual display 46 may be integrated with the control unit 44. In some embodiments, the one or more control devices may be separate and/or spaced apart from the control unit 44. In some embodiments, the one or more control devices may be integrated with the control unit 44. In some embodiments, the control unit 44 may comprise a touch screen display. In some embodiments, the visual display 46 and/or the one or more controller devices may be and/or may be integrated with the touch screen display. Other configurations are also contemplated.

In some embodiments, the control unit 44 may include, among other suitable components, a processor, memory, and/or an input/output (I/O) unit. The processor of the control unit 44 may include a single processor or more than one processor working individually or with one another. The processor may be configured to execute instructions, including instructions that may be loaded into the memory. Some example processor components may include, but are not limited to, microprocessors, microcontrollers, multi-core processors, graphical processing units, digital signal processors, application specific integrated circuits (ASICs), field programmable gate arrays (FPGAs), discrete circuitry, and/or other suitable types of data processing devices.

The memory of the control unit 44 may include a single memory component or more than one memory component each working individually or with one another. Some example types of memory may include random access memory (RAM), EEPROM, FLASH, suitable volatile storage devices, suitable non-volatile storage devices, persistent memory (e.g., read only memory (ROM), hard drive, Flash memory, optical disc memory, and/or other suitable persistent memory) and/or other suitable types of memory. The memory may be or may include a non-transitory computer readable medium.

The I/O unit of the control unit 44 may include a single I/O component or more than one I/O component each working individually or with one another. Some example I/O units may be any type of communication port configured to communicate with other components of the building management system. Example types of I/O units may include wired ports, wireless ports, radio frequency (RF)

ports, Low-Energy Bluetooth ports, Bluetooth ports, Near-Field Communication (NFC) ports, HDMI ports, Wi-Fi ports, Ethernet ports, VGA ports, serial ports, parallel ports, component video ports, S-video ports, composite audio/video ports, DVI ports, USB ports, optical ports, and/or other suitable ports.

In some embodiments, the control unit 44 may be in communication with various components of the extracorporeal perfusion system 10. For example, FIG. 1 illustrates that the control unit 44 may be in communication (e.g., wireless, wired communication, or other communication means capable of transmitting signals) with the clamp 26, the flow sensor 22, the pressure sensor 24, and/or the roller pump 28. FIG. 1 depicts the flow sensor 22 in communication with the control unit 44 via a dashed line 30. FIG. 1 depicts the pressure sensor 24 in communication with the control unit 44 via a dashed line 32. FIG. 1 depicts the clamp 26 in communication with the control unit 44 via a dashed line 48. FIG. 1 depicts the roller pump 28 in communication with the control unit 44 via a dashed line 29. In some embodiments, the control unit 44 may be in communication with other components, devices, sensors, etc. whether explicitly depicted or not.

In some embodiments, the control unit 44 may be integrated into a console or workstation of the extracorporeal perfusion system 10. In some embodiments, the control unit 44 may be integrated directly into a heart-lung machine (HLM). The control unit 44 may be in direct or indirect communication with a console, a workstation, and/or an HLM.

Further, the clamp 26, the flow sensor 22, the pressure sensor 24, the roller pump 28, and/or the control unit 44 may together form a closed-loop system capable of automatically or manually regulating the flow rate of fluid (e.g., blood, priming fluid, etc.) within the venous fluid pathway 34 and/or the arterial fluid pathway 42. In some embodiments, the flow rate within the venous fluid pathway 34 and/or the arterial fluid pathway 42 may be from 0-8 liters/min at a pressure between −200 mmHg and +800 mmHg. Other configurations are also contemplated.

In some embodiments, the flow sensor 22 and/or the pressure sensor 24 may be configured to sense a first parameter (e.g., flow rate, pressure etc.) of fluid (e.g., blood, priming fluid, etc.) passing through the extracorporeal perfusion system 10, the venous fluid pathway 34, and/or the arterial fluid pathway 42. In some embodiments, the flow sensor 22 and/or the pressure sensor 24 may be configured to transmit a signal corresponding to the sensed parameter (e.g., flow rate, pressure, etc.) to the control unit 44. Further, the control unit 44 may be configured to receive the signal (corresponding to the sensed flow rate and/or pressure of the fluid (e.g., blood, priming fluid, etc.) within the extracorporeal perfusion system 10, the venous fluid pathway 34, and/or the arterial fluid pathway 42) transmitted by the flow sensor 22 and/or the pressure sensor 24. The control unit 44 may be configured to compare the signal received from the flow sensor 22 and/or the pressure sensor 24 to a parameter (e.g., flow rate, pressure, etc.) set point input by a clinician into the control unit 44. After comparing the signal received from the flow sensor 22 and/or the pressure sensor 24, the control unit 44 may transmit a signal to the clamp 26. The clamp 26 may be configured to receive the signal transmitted by and/or from the control unit 44. After receiving and processing the signal transmitted by and/or from the control unit 44, the clamp 26 may be automatically actuated to adjust the fluid flow (e.g., the flow rate of the fluid (e.g., blood, priming fluid, etc.)) through the extracorporeal perfusion system 10, the venous fluid pathway 34, and/or the arterial fluid pathway 42 in response to receiving the signal transmitted by and/or from the control unit 44. In some embodiments, the clamp 26 may send a confirmation signal back to the control unit 44 confirming the position to which the aperture of the clamp 26 has been actuated (e.g., the clamp 26 may send a signal indicating the size of the aperture through which the fluid (e.g., blood, priming fluid, etc.) is flowing, such as a percentage that the clamp 26 is open or closed).

In some embodiments, a component (e.g., control unit 44, clamp 26, flow sensor 22, pressure sensor 24, etc.) of the extracorporeal perfusion system 10 may include an algorithm which utilizes the sensed flow rate data from the flow sensor 22 and/or sensed pressure data from the pressure sensor 24 to calculate the appropriate automatic actuation of the clamp 26 required to meet the clinician's desired fluid flow rate within the venous fluid pathway 34 and/or the arterial fluid pathway 42. It can be further appreciated that the set point and/or set range of values for the flow rate of fluid (e.g., blood, priming fluid, etc.) through the venous fluid pathway 34 may be input by a clinician via the control features (e.g., display, dial, button, etc.) 46 of the control unit 44 or other components of the extracorporeal perfusion system 10. In other words, a clinician may be able to input a set point or a set range of values for flow rates in various fluid pathways in the system via a touchpad, dial, control knob, etc.

In some embodiments, after receiving and processing the signal from the control unit 44, the clamp 26 may be automatically actuated to adjust the fluid flow rate through the venous fluid pathway 34 and/or the arterial fluid pathway 42 in response to receiving the signal from the control unit 44. In some embodiments, a component (e.g., control unit 44, clamp 26, flow sensor 22, pressure sensor 24, etc.) of the extracorporeal perfusion system 10 may include an algorithm which utilizes sensed pressure data from the pressure sensor 24 to calculate the appropriate automatic actuation of the clamp 26 required to meet the clinician's desired fluid pressure within the venous fluid pathway 34 and/or the arterial fluid pathway 42. It can be appreciated that the set point or set range of values for the pressure of fluid (e.g., blood, priming fluid, etc.) through the venous fluid pathway 34 and/or the arterial fluid pathway 42 may be input by a clinician via the visual display 46 of the control unit 44. In other words, a clinician may be able to input a set point or set range of values for fluid pressure in various fluid pathways in the system via a touchpad, dial, control knob, etc.

In some embodiments, the control unit 44 (and all control units described herein) may permit a user (e.g., perfusionist, clinician, etc.) to input pre-defined values or a pre-defined range of values for the flow rate of fluid (e.g., blood, priming fluid, etc.) within the venous fluid pathway 34 (independent of the arterial fluid pathway 42), the arterial fluid pathway 42 (independent of the venous fluid pathway 34), or both the venous fluid pathway 34 and the arterial fluid pathway 42.

In some alternative embodiments, extracorporeal perfusion system 10, the venous fluid pathway 34, and/or the fluid reservoir 18 may comprise a vacuum unit (not shown) disposed along, coupled to, and/or in communication with the venous fluid pathway 34 and/or the fluid reservoir 18. In some embodiments, the vacuum unit may be in fluid communication with the venous fluid pathway 34, the fluid reservoir 18, and/or fluid (e.g., blood, priming fluid, etc.) disposed and/or flowing therein. In some embodiments, the vacuum unit may be disposed upstream of the fluid reservoir 18. In some embodiments, the vacuum unit may be disposed adjacent to and/or in communication with the fluid reservoir 18. In some embodiments, the vacuum unit may be directly coupled to the fluid reservoir 18. In some embodiments, the vacuum unit may be disposed within the fluid reservoir 18. In some embodiments, the vacuum unit may be integrated with the fluid reservoir 18. In some embodiments, the vacuum unit may be spaced apart from the fluid reservoir 18. Other configurations are also contemplated.

In some embodiments, the vacuum unit may be in communication (e.g., electronic communication, wired communication, wireless communication, etc.) with the control unit 44. In some embodiments, the vacuum unit may be configured to generate negative pressure along and/or within the venous fluid pathway 34 and/or the fluid reservoir 18, thereby generating and/or enhancing the flow of fluid (e.g., blood, priming fluid, etc.) from the patient's vasculature and/or from the at least one venous portion of the patient's vasculature to the fluid reservoir 18, and/or within the venous fluid pathway 34. In some embodiments, the vacuum unit may be utilized in conjunction with a gravitational flow system, while in other embodiments, the vacuum unit may be utilized without a gravitational flow system.

In some embodiments, the control unit 44 may be configured to adjust the vacuum unit based on the signals received from various sensors within the extracorporeal perfusion system 10. For example, a user may set the control unit 44 to maintain a desired flow rate within the extracorporeal perfusion system 10, the venous fluid pathway 34, and/or the arterial fluid pathway 42. Other configurations are also contemplated.

In some embodiments, the oxygenator 20 may include a housing having multiple chambers or pathways separated by a semi-permeable membrane, whereby fluid (e.g., blood, priming fluid, etc.) may flow through one chamber or pathway, while a compressed air and oxygen gas mixture flows through another chamber or pathway. The semi-permeable membrane may include multiple microporous hollow fibers, each fiber having a lumen extending therethrough through which the compressed air and oxygen gas mixture flows. Gas exchange may occur via diffusion of the gases across the multiple microporous hollow fibers, whereby oxygen moves from the inside of the multiple microporous hollow fibers into the fluid (e.g., blood, priming fluid, etc.) while carbon dioxide diffuses from the fluid (e.g., blood, priming fluid, etc.) into the interior of the multiple microporous hollow fibers, where it is swept away by the compressed air and oxygen gas mixture flowing through the multiple microporous hollow fibers. This gas exchange allows for oxygenation of fluid (e.g., blood, priming fluid, etc.) and removal of carbon dioxide.

The oxygenator 20 may be disposed downstream of the fluid reservoir 18. In some embodiments, the oxygenator 20 may be disposed downstream of the roller pump 28. In some embodiments, the fluid reservoir 18 and the oxygenator 20 may be integrated and/or combined into a single unit. In some embodiments, the fluid reservoir 18 and the oxygenator 20 may be separate units and/or structures that are fluidly coupled to together as shown in FIG. 1. Other configurations are also contemplated.

In some embodiments, the extracorporeal perfusion system 10 and/or the oxygenator 20 may comprise a heat exchanger (not shown) configured to heat and/or cool fluid (e.g., blood, priming fluid, etc.) flowing therethrough prior to returning the fluid (e.g., blood, priming fluid, etc.) to the patient's vasculature (e.g., the aorta 16). In some embodiments, the heat exchanger may be integrated with the oxygenator 20. In some embodiments, the oxygenator 20 and/or the heat exchanger may be coupled to and/or may be in fluid communication with the fluid reservoir 18 via the flexible tubing 19. In some embodiments, the fluid reservoir 18, the oxygenator 20, and/or the heat exchanger may be integrated and/or combined into a single unit. In some embodiments, the oxygenator 20 and/or the heat exchanger may be integrated and/or combined into a single unit, while the fluid reservoir 18 is a separate unit and/or structure that is fluidly coupled to the single unit comprising the oxygenator 20 and the heat exchanger. Other configurations are also contemplated.

In some embodiments, the clamp 26 may be an electronic remote clamp (ERC). In some embodiments, the clamp 26 may be in communication (e.g., electronic communication, wired communication, wireless communication, etc.) with the control unit 44. In some embodiments, the control unit 44 may be configured to control and/or regulate fluid flow along and/or within the venous fluid pathway 34 and/or the arterial fluid pathway 42 (e.g., the tubing) using the clamp 26, and signals from the sensor(s) disclosed herein. In some embodiments, the control unit 44 may be configured to actuate the clamp 26 to change the cross-sectional area of the lumen of the venous fluid pathway 34 and/or the arterial fluid pathway 42 (e.g., the tubing) to increase and/or reduce the cross-sectional area of the lumen of the venous fluid pathway 34 and/or the arterial fluid pathway 42 (e.g., the tubing) and thereby change and/or affect fluid flow within the venous fluid pathway 34 and/or the arterial fluid pathway 42 (e.g., the tubing). In some embodiments, the clamp 26 may be configured to and/or may be capable of completely closing off the lumen of the venous fluid pathway 34 and/or the arterial fluid pathway 42 (e.g., the tubing), thereby stopping fluid flow within the venous fluid pathway 34 and/or the arterial fluid pathway 42 (e.g., the tubing) and/or the extracorporeal perfusion system 10. In some embodiments, the clamp 26 may be a manually operated and/or actuated clamp and control of the clamp 26 may be performed manually by a user or clinician. Other configurations are also contemplated.

In some alternative configurations, the extracorporeal perfusion system 10 may comprise a plurality of clamps disposed along, coupled to, and/or in communication with the venous fluid pathway 34 and/or the arterial fluid pathway 42 (e.g., the tubing). The plurality of clamps may be in communication (e.g., electronic communication, wired communication, wireless communication, etc.) with the control unit 44, and the control unit 44 may be configured to control and/or regulate fluid flow along and/or within the venous fluid pathway 34 and/or the arterial fluid pathway 42 (e.g., the tubing) using the plurality of clamps.

In some embodiments, the roller pump 28 may be disposed along, coupled to, and/or in communication with the arterial fluid pathway 42 and/or the flexible tubing 19 downstream of the fluid reservoir 18 and/or upstream of the oxygenator 20. In some embodiments, the roller pump 28 may be disposed completely external to the arterial fluid pathway 42 and/or the flexible tubing 19 and/or may be devoid of fluid communication with the fluid (e.g., blood, priming fluid, etc.) flowing within the arterial fluid pathway 42 and/or the flexible tubing 19.

In some embodiments, the roller pump 28 may be in communication (e.g., electronic communication, wired communication, wireless communication, etc.) with the control unit 44. In some embodiments, the control unit 44 may be configured to generate fluid flow and/or pressure along and/or within the arterial fluid pathway 42 and/or the flexible tubing 19 using the roller pump 28, thereby causing the flow of fluid (e.g., blood, priming fluid, etc.) within the arterial fluid pathway 42 and/or the flexible tubing 19 and/or from the fluid reservoir 18 to the oxygenator 20 and beyond. It can be appreciated that the function of the roller pump 28 is to generate blood flow within the extracorporeal perfusion system 10 (e.g., circulate fluid (e.g., blood, priming fluid, etc.) from the patient to the oxygenator 20 and back to the patient) and to also generate blood pressure and facilitate blood flow within the patient's vasculature.

In some embodiments, the control unit 44 may be configured to generate fluid flow and/or pressure along and/or within the venous fluid pathway 34 and/or the arterial fluid pathway 42 using the roller pump 28, thereby causing the flow of fluid (e.g., blood, priming fluid, etc.) within the venous fluid pathway 34 and/or the arterial fluid pathway 42 downstream of and/or from the fluid reservoir 18, through the oxygenator 20, and/or to the arterial portion of the patient's vasculature (e.g., the aorta 16). Other configurations are also contemplated.

Figure 2:
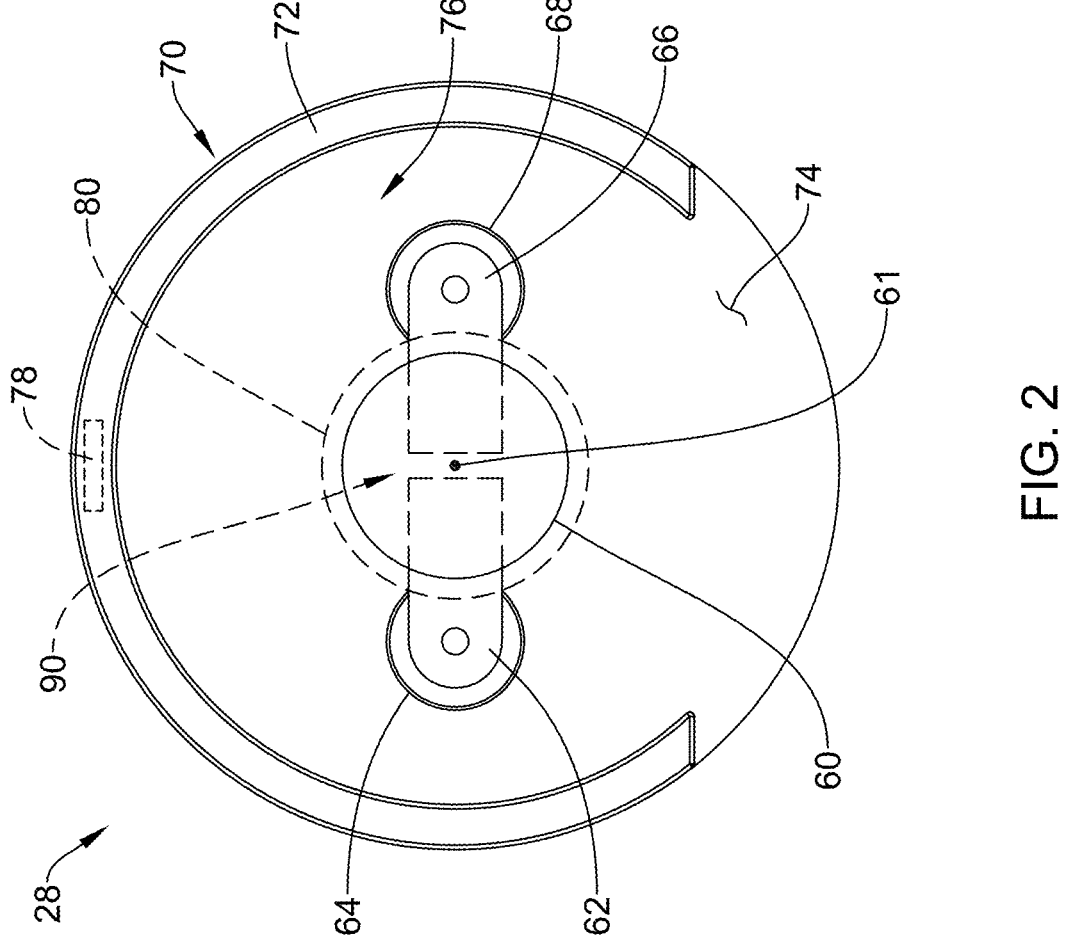
FIGS. 2-3 schematically illustrate selected aspects of a roller pump in accordance with the disclosure.
Figure 3:
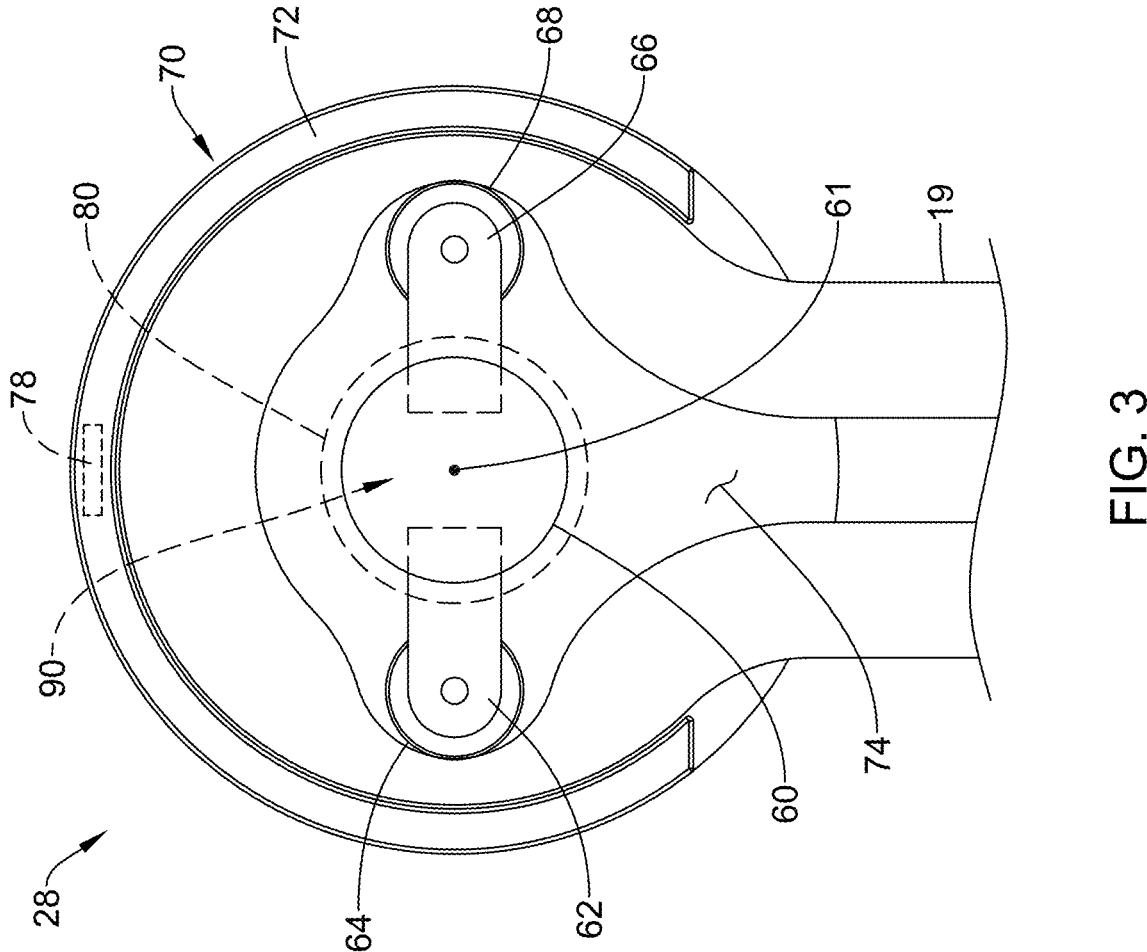

Some additional aspects of the roller pump 28 will be described with respect to FIGS. 2-10. FIGS. 2-3 schematically illustrate selected aspects that may be considered generic and/or may apply to all disclosed embodiments of the roller pump 28. FIGS. 4-10 schematically illustrate selected aspects of various embodiments of the roller pump 28 and/or an electronic actuator thereof, as discussed herein.

Turning now to FIGS. 2-3, the roller pump 28 may comprise a roller pump rotor 60 comprising a first roller arm 62 having a first roller 64 rotatably coupled thereto and a second roller arm 66 having a second roller 68 rotatably coupled thereto. In some alternative embodiments, the roller pump 28 may comprise one or more additional roller arms and associated rollers rotatably coupled thereto. The first roller arm 62 (and the first roller 64) and the second roller arm 66 (and the second roller 68) may be movable relative to the roller pump rotor 60 and/or a central axis 61 of the roller pump rotor 60. In at least some embodiments, the first roller arm 62 and the second roller arm 66 may be movable radially relative to the roller pump rotor 60 and/or the central axis 61 of the roller pump rotor 60. In some embodiments, the first roller arm 62 and the second roller arm 66 may be movable radially outward from and/or radially inward toward the roller pump rotor 60 and/or the central axis 61 of the roller pump rotor 60.

In some embodiments, the first roller arm 62 may be rotatably coupled to the first roller 64 above the first roller 64. In some embodiments, the first roller arm 62 may be rotatably coupled to the first roller 64 below the first roller 64. In some embodiments, the first roller arm 62 may be rotatably coupled to the first roller 64 above and below the first roller 64. In some embodiments, the second roller arm 66 may be rotatably coupled to the second roller 68 above the second roller 68. In some embodiments, the second roller arm 66 may be rotatably coupled to the second roller 68 below the second roller 68. In some embodiments, the second roller arm 66 may be rotatably coupled to the second roller 68 above and below the second roller 68. Other configurations are also contemplated.

In some embodiments, the roller pump 28 may comprise a raceway 70 disposed around the roller pump rotor 60 and configured to receive the flexible tubing 19. In some embodiments, the raceway 70 may comprise an outer wall 72 radially spaced apart from the roller pump rotor 60 and a floor 74 extending from the roller pump rotor 60 to the outer wall 72 to define and/or form a channel 76 extending circumferentially around the roller pump rotor 60. In at least some embodiments, the channel 76 may be sized and configured to receive the flexible tubing 19, as seen in FIG. 3.

In some embodiments, the first roller arm 62 and the second roller arm 66 may be movable radially inward toward the roller pump rotor 60 and/or the central axis 61 of the roller pump rotor 60 such that at least a portion of the first roller 64 and the second roller 68 may be disposed radially inward of an outer perimeter of the roller pump rotor 60, to accommodate loading of the flexible tubing 19 into the raceway 70 and/or the channel 76 in a parking position, for example. In some embodiments, the first roller arm 62 and the second roller arm 66 may be movable radially inward toward the roller pump rotor 60 and/or the central axis 61 of the roller pump rotor 60 such that at least a portion of the first roller 64 and the second roller 68 may be recessed within the roller pump rotor 60, to accommodate loading of the flexible tubing 19 into the raceway 70 and/or the channel 76 in the parking position, for example. The use and/or existence of the parking position may permit the roller pump 28 to be made in a smaller overall package by saving space therein.

In some embodiments, the first roller arm 62 and the second roller arm 66 may be movable radially outward from the roller pump rotor 60 and/or the central axis 61 of the roller pump rotor 60 such that the first roller 64 and the second roller 68 may be disposed in contact with the outer wall 72 of the raceway 70 in a full occlusion position for example. In some embodiments, the first roller arm 62 and the second roller arm 66 may be movable radially outward from the roller pump rotor 60 and/or the central axis 61 of the roller pump rotor 60 such that the first roller 64 and the second roller 68 may be disposed in contact with the flexible tubing 19 disposed within the raceway 70 and/or the channel 76.

In some embodiments, the outer wall 72 may extend circumferentially around at least 50% of a circumference of the roller pump rotor 60. In some embodiments, the outer wall 72 may extend circumferentially around at least 60% of the circumference of the roller pump rotor 60. In some embodiments, the outer wall 72 may extend circumferentially around at least 70% of the circumference of the roller pump rotor 60. In some embodiments, the outer wall 72 may extend circumferentially around at least 75% of the circumference of the roller pump rotor 60. Other configurations are also contemplated.

In some embodiments, the floor 74 may be solid, as illustrated. In some alternative embodiments, the floor 74 may be intermittent and/or discontinuous (e.g., slotted, apertures formed in and/or extending therethrough, etc.). In at least some embodiments, the floor 74 may extend completely around the circumference of the roller pump rotor 60. Other configurations are also contemplated.

The roller pump 28 may comprise a pump motor 80 configured to rotate the roller pump rotor 60 relative to the raceway 70. In some embodiments, the pump motor 80 may be fixedly attached to the raceway 70 and/or the floor 74. In some embodiments, the pump motor 80 may be disposed below the raceway 70 and/or the floor 74. For example, in the view shown in FIGS. 2-3, the pump motor 80 is disposed behind the raceway 70 and/or the floor 74 (extending away from the viewer), and thus is shown with hidden lines. Other configurations are also contemplated. In some embodiments, the pump motor 80 may be disposed coaxially with the central axis 61 of the roller pump rotor 60. Other configurations are also contemplated.

In some embodiments, the pump motor 80 and/or the roller pump rotor 60 may be configured to rotate the first roller arm 62 and the second roller arm 66 relative to the raceway 70 and/or around the central axis 61 of the roller pump rotor 60 to generate flow within the flexible tubing 19 and/or the extracorporeal perfusion system 10 (e.g., FIG. 1) in the direction of rotation when the flexible tubing 19 is at least partially compressed and/or at least partially occluded. The pump motor 80 may be operatively engaged with the roller pump rotor 60, and/or the first roller arm 62 and the second roller arm 66, such as via one or more shafts, gears, drive mechanisms, etc.

In some embodiments, the roller pump 28 may comprise an electronic actuator 90 disposed on and/or coupled to the roller pump rotor 60. In some embodiments, the electronic actuator 90 may be configured to change a radial position of the first roller 64 and the second roller 68 relative to the central axis 61 of the roller pump rotor 60 and/or relative to the outer wall 72 of the raceway 70. In at least some embodiments, with the flexible tubing 19 disposed within the raceway 70 (e.g., FIG. 3), the radial position of the first roller 64 and the second roller 68 may correspond to a degree of occlusion and/or a degree of compression of the flexible tubing 19. As the radial position of the first roller 64 and the second roller 68 moves radially outward and/or away from the central axis 61 of the roller pump rotor 60, and/or toward the outer wall 72 of the raceway 70, the degree of occlusion of the flexible tubing 19 increases. Similarly, as the radial position of the first roller 64 and the second roller 68 moves radially inward and/or toward the central axis 61 of the roller pump rotor 60, and/or away from the outer wall 72 of the raceway 70, the degree of occlusion of the flexible tubing 19 decreases.

In at least some embodiments, the electronic actuator 90 may function independently of the pump motor 80 to change the radial position of the first roller 64 and the second roller 68 relative to the central axis 61 of the roller pump rotor 60 and/or relative to the outer wall 72 of the raceway 70. In some embodiments, the electronic actuator 90 may be configured to change the radial position of the first roller 64 and the second roller 68 relative to the central axis 61 of the roller pump rotor 60 and/or relative to the outer wall 72 of the raceway 70 while the pump motor 80 is rotating the roller pump rotor 60 relative to the raceway 70. In some embodiments, the electronic actuator 90 may be configured to change the radial position of the first roller 64 and the second roller 68 relative to the central axis 61 of the roller pump rotor 60 and/or relative to the outer wall 72 of the raceway 70 without shutting down the pump motor 80 and/or while the pump motor 80 is running.

In some embodiments, the electronic actuator 90 may be configured to automatically change the radial position of the first roller 64 and the second roller 68 relative to the central axis 61 of the roller pump rotor 60 and/or relative to the outer wall 72 of the raceway 70 in order to maintain a desired flow rate through the flexible tubing 19. In some embodiments, the electronic actuator 90 may be configured to automatically change the radial position of the first roller 64 and the second roller 68 relative to the central axis 61 of the roller pump rotor 60 and/or relative to the outer wall 72 of the raceway 70 in response to flow rate of fluid measured within the extracorporeal perfusion system 10 and/or the flexible tubing 19 (such as by the flow sensor 22). In some embodiments, the electronic actuator 90 may be configured to automatically change the radial position of the first roller 64 and the second roller 68 relative to the central axis 61 of the roller pump rotor 60 and/or relative to the outer wall 72 of the raceway 70 in response to pressure of fluid measured within the extracorporeal perfusion system 10 and/or the flexible tubing 19 (such as by the pressure sensor 24).

In some embodiments, the raceway 70 may comprise a force sensor 78 configured to sense force exerted against the flexible tubing 19 and/or the outer wall 72 of the raceway 70 by the first roller 64 and the second roller 68. In some embodiments, the force sensor 78 may be disposed within the outer wall 72 of the raceway 70. In some embodiments, the force sensor 78 may be secured to the outer wall 72 of the raceway 70. In some embodiments, the force sensor 78 may recessed within the outer wall 72 of the raceway 70. In some embodiments, the force sensor 78 may be disposed within the first roller 64 and/or the second roller 68. In some embodiments, the force sensor 78 may be exposed to and/or face towards the channel 76. Other configurations are also contemplated.

Turning now to FIGS. 4-10, selected aspects of several embodiments of the roller pump 28 are illustrated. In some embodiments, the roller pump 28 may comprise a threaded mechanism configured to engage the first roller arm 62 and the second roller arm 66 such that rotation and/or actuation of the threaded mechanism, such as by the electronic actuator 90, changes the radial position of the first roller 64 and the second roller 68 relative to the central axis 61 of the roller pump rotor 60 and/or relative to the outer wall 72 of the raceway 70. In some embodiments, the threaded mechanism may be a component of the electronic actuator 90 itself. In some embodiments, the threaded mechanism may be operatively coupled to the electronic actuator 90. In at least some embodiments, the electronic actuator 90 and/or the threaded mechanism may be entirely self-contained within the roller pump rotor 60. Other configurations are also contemplated.

Figure 4:
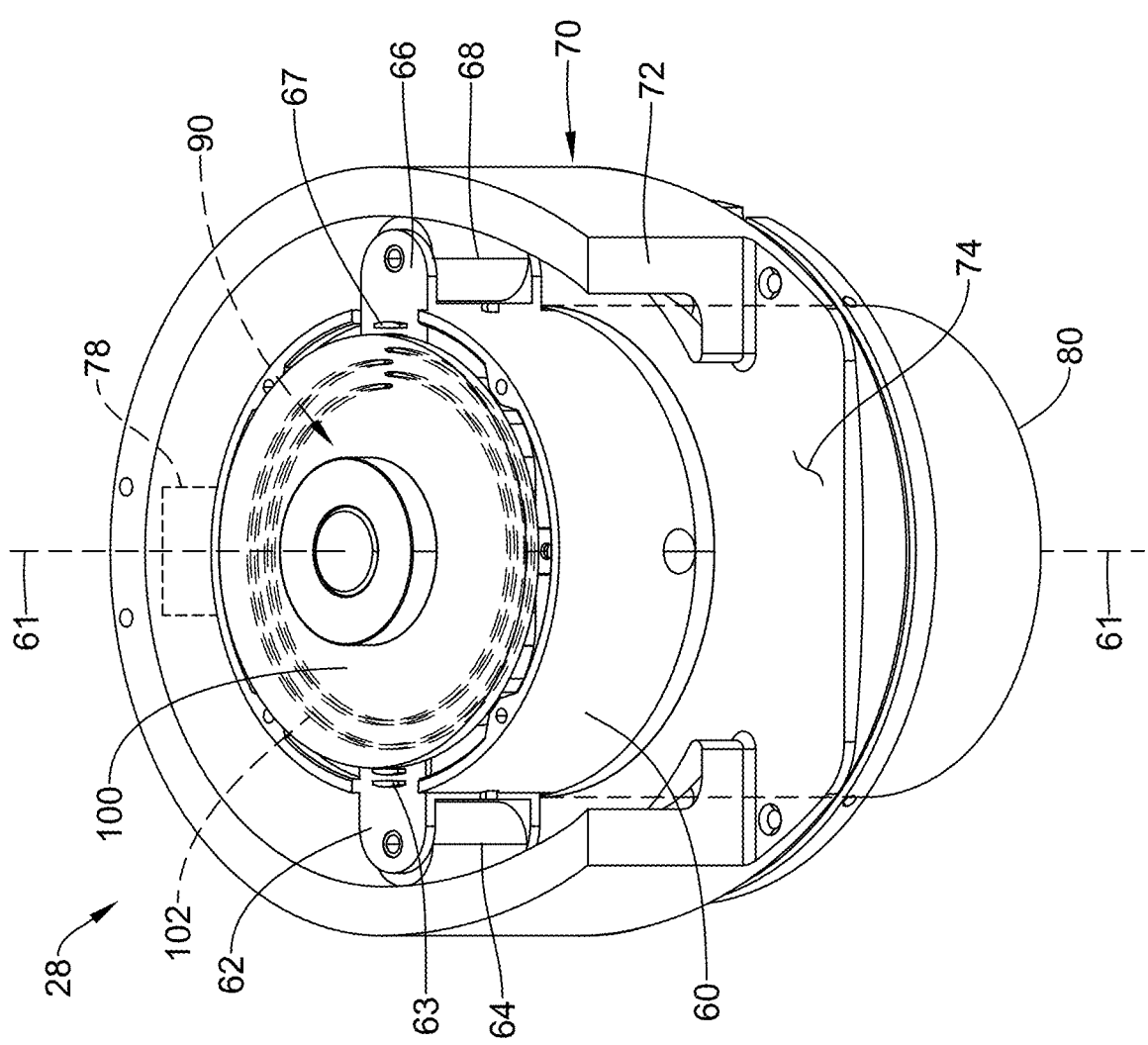
FIG. 4 schematically illustrates selected aspects of a roller pump in accordance with the disclosure.

In some embodiments, the threaded mechanism may comprise a flattened disk 100 having a center and a peripheral edge, as seen in FIG. 4. The center of the flattened disk 100 may be positioned on and/or may be coaxial with the central axis 61 of the roller pump rotor 60. The threaded mechanism and/or the flattened disk 100 may comprise a spiral thread 102 extending radially between the center of the flattened disk 100 and the peripheral edge of the flattened disk 100. The spiral thread 102 may extend from the flattened disk 100 in a direction parallel to the central axis 61 of the roller pump rotor 60. For example, in the view shown in FIG. 4, the spiral thread 102 extends downward from the flattened disk 100 and/or toward the pump motor 80. In some embodiments, the spiral thread 102 may be continuous from its radially innermost extent to its radially outermost extent. In some embodiments, the spiral thread 102 may be discontinuous from its radially innermost extent to its radially outermost extent. In some embodiments, the spiral thread 102 may comprise a plurality of individual spiral threads and/or a plurality of distinct spiral threads. Other configurations are also contemplated.

The first roller arm 62 may comprise threads 63 configured to engage with and/or cooperate with the spiral thread 102 of the threaded mechanism and/or the flattened disk 100 and the second roller arm 66 may comprise threads 67 configured to engage with and/or cooperate with the spiral thread 102 of the threaded mechanism and/or the flattened disk 100. In some embodiments, the threads 63 of the first roller arm 62 and/or the threads 67 of the second roller arm 66 may be curved and/or formed in a complimentary manner to the spiral thread 102 of the threaded mechanism and/or the flattened disk 100. Other configurations are also contemplated.

The flattened disk 100 may be configured to operatively couple the electronic actuator 90 to the first roller arm 62 and the second roller arm 66. In some embodiments, as the electronic actuator 90 rotates and/or actuates the threaded mechanism and/or the flattened disk 100, the spiral thread 102 may engage with and/or cooperate with the threads 63 of the first roller arm 62 and/or the threads 67 of the second roller arm 66 to move the first roller arm 62 and the second roller arm 66, and/or to change the radial position of the first roller 64 and the second roller 68, relative to the central axis 61 of the roller pump rotor 60 and/or relative to the outer wall 72 of the raceway 70.

In some embodiments, the roller pump 28 and/or the threaded mechanism may comprise a second flattened disk (not shown) having a center and a peripheral edge, similar in structure to the flattened disk 100 shown in FIG. 4. The center of the second flattened disk may be positioned on and/or may be coaxial with the central axis 61 of the roller pump rotor 60. The second flattened disk may be disposed opposite the flattened disk 100 relative to the roller pump rotor 60 and/or the first roller arm 62 and the second roller arm 66. For example, in the view shown in FIG. 4, the flattened disk 100 is disposed above the first roller arm 62 and the second roller arm 66, and the second flattened disk may be disposed below the first roller arm 62 and the second roller arm 66. Other configurations are also contemplated.

The second flattened disk may comprise a second spiral thread (not shown) extending radially between the center of the second flattened disk and the peripheral edge of the second flattened disk. The second spiral thread may extend from the second flattened disk in a direction parallel to the central axis 61 of the roller pump rotor 60. In some embodiments, the second spiral thread may extend from the second flattened disk in a second direction opposite the direction parallel to the central axis 61 of the roller pump rotor 60 that the spiral thread 102 extends. For example, in the view shown in FIG. 4, the second spiral thread may extend upward from the second flattened disk and/or away from the pump motor 80. In some embodiments, the second spiral thread may be continuous from its radially innermost extent to its radially outermost extent. In some embodiments, the second spiral thread may be discontinuous from its radially innermost extent to its radially outermost extent. In some embodiments, the second spiral thread may comprise a plurality of individual spiral threads and/or a plurality of distinct spiral threads. Other configurations are also contemplated.

In embodiments where the roller pump 28 and/or the threaded mechanism comprises a second flattened disk, the first roller arm 62 may comprise second threads configured to engage with the second spiral thread of the second flattened disk, wherein the second threads of the first roller arm 62 may be disposed opposite the threads 63 with respect to the first roller arm 62, and the second roller arm 66 may comprise second threads configured to engage with and/or cooperate with the second spiral thread of the second flattened disk, wherein the second threads of the second roller arm 66 may be disposed opposite the threads 67 with respect to the second roller arm 66. In some embodiments, the second threads of the first roller arm 62 and/or the second threads of the second roller arm 66 may be curved and/or formed in a complimentary manner to the second spiral thread of the second flattened disk. Other configurations are also contemplated.

Figure 5:
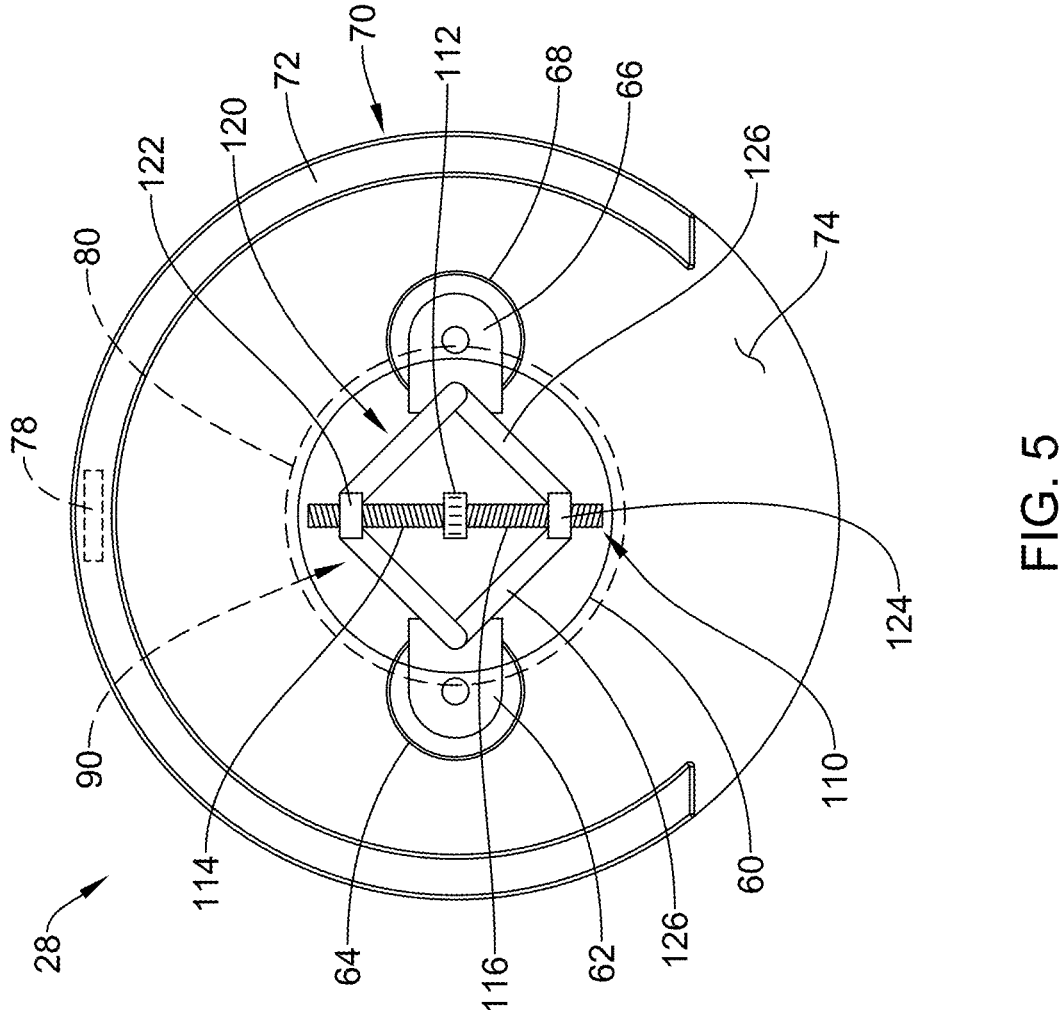
FIG. 5 schematically illustrates selected aspects of a roller pump in accordance with the disclosure.

In some embodiments, the threaded mechanism may comprise a threaded rod 110 and a scissors assembly 120, as seen schematically in FIG. 5. The threaded rod 110 may be operatively coupled to the electronic actuator 90. In some embodiments, the threaded rod 110 may comprise a central gear 112 fixedly secured thereto, wherein the central gear 112 is configured to operatively engage with the electronic actuator 90. The threaded rod 110 may comprise first threads 114 extending in a first helical direction around the threaded rod 110 and second threads 116 extending in a second helical direction opposite the first helical direction around the threaded rod 110. Other configurations are also contemplated.

The scissors assembly 120 may comprise a first hub 122 engaged with the first threads 114 and a second hub 124 engaged with the second threads 116. As the threaded rod 110 rotates, the first hub 122 and the second hub 124 may be configured to translate along the threaded rod 110 in opposite directions (e.g., towards each other or away from each other). The scissors assembly 120 may comprise a plurality of linkages 126 coupling the first hub 122 and the second hub 124 to the first roller arm 62 and the second roller arm 66. The plurality of linkages 126 may be pivotably coupled to the first roller arm 62 and the second roller arm 66. In some embodiments, the plurality of linkages 126 may be pivotably coupled to the first hub 122 and the second hub 124. In some embodiments, the plurality of linkages 126 may comprise additional linkages, additional individual links and/or segments, etc. beyond those expressly illustrated in FIG. 5. Other configurations are also contemplated.

The threaded rod 110 and the scissors assembly 120 may be configured to operatively couple the electronic actuator 90 to the first roller arm 62 and the second roller arm 66. As the threaded rod 110 rotates (e.g., via activation of the electronic actuator 90, etc.) to translate the first hub 122 and the second hub 124 along the threaded rod 110, the first roller arm 62 and the second roller arm 66 may be moved radially relative to the roller pump rotor 60 and/or the central axis 61 (not shown in FIG. 5) of the roller pump rotor 60 to change the radial position of the first roller 64 and the second roller 68 relative to the central axis 61 of the roller pump rotor 60.

Figure 6:
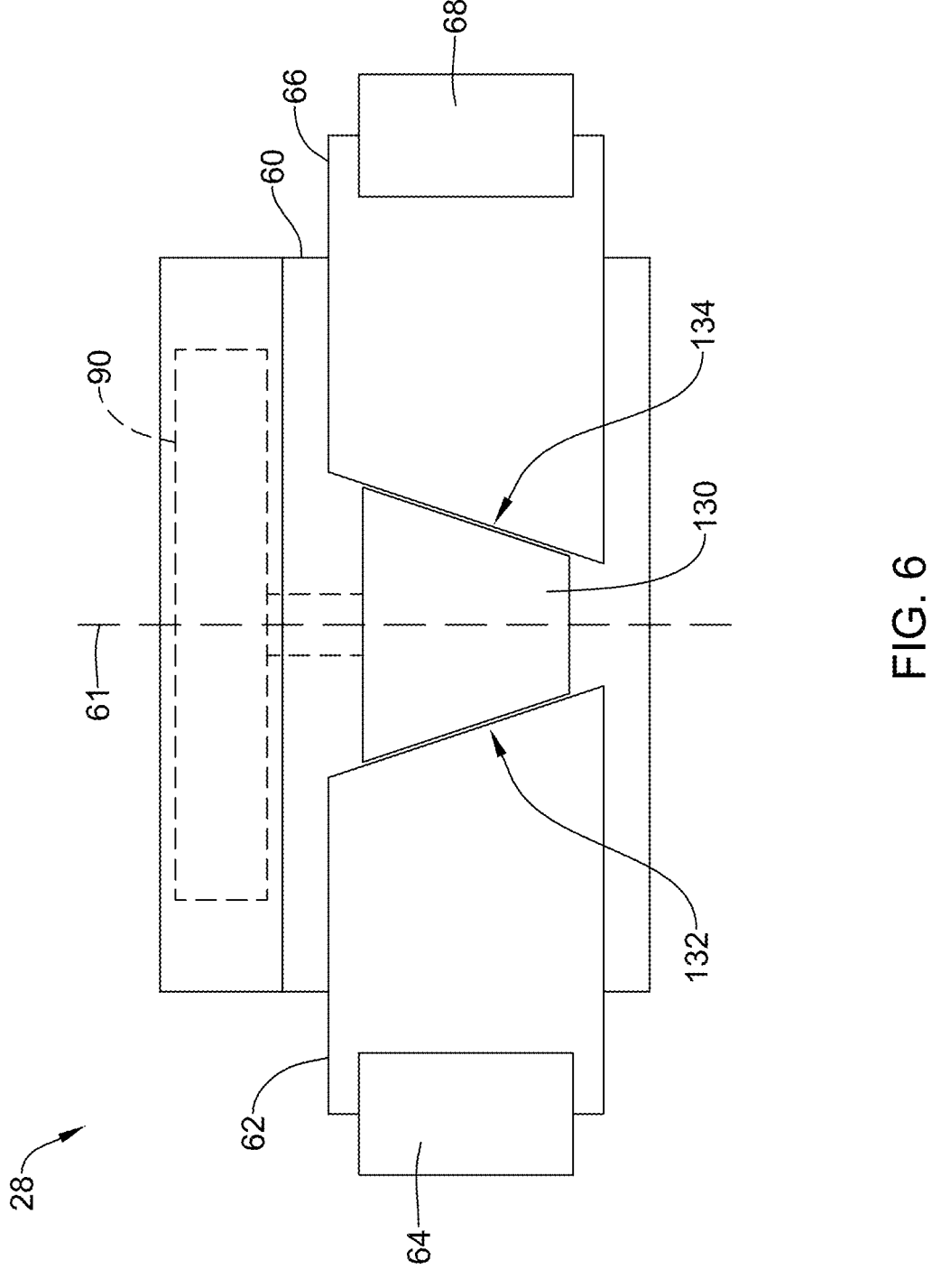
FIG. 6 schematically illustrates selected aspects of a roller pump in accordance with the disclosure.

FIG. 6 schematically illustrates selected aspects of another embodiment of the roller pump 28. In the interest of clarity, some features of the roller pump 28 are not shown. FIGS. 2-3 may be referred to for elements that are not expressly illustrated in FIG. 6. In some embodiments, the electronic actuator 90 may comprise and/or may be operatively coupled to a wedge 130 configured to move and/or translate perpendicularly to the first roller arm 62 and the second roller arm 66 to change the radial position of the first roller 64 and the second roller 68 relative to the central axis 61 of the roller pump rotor 60. In some embodiments, the wedge 130 may be configured to translate parallel to the central axis 61 of the roller pump rotor 60 via actuation of the electronic actuator 90. In some embodiments, the wedge 130 may be configured to translate axially along the central axis 61 of the roller pump rotor 60 via actuation of the electronic actuator 90. The first roller arm 62 may comprise a first angled surface 132 configured to engage with the wedge 130. The second roller arm 66 may comprise a second angled surface 134 configured to engage with the wedge 130. As the electronic actuator 90 translates the wedge 130 toward the floor 74 of the raceway 70 (not shown, but downward in the view shown in FIG. 6), the wedge 130 may engage with the first angled surface 132 and the second angled surface 134 to move the first roller arm 62 and the second roller arm 66 radially outward relative to the roller pump rotor 60 and/or toward the outer wall 72 (not shown) of the raceway 70. Actuation of the electronic actuator 90 in an opposite and/or reverse direction may translate the wedge 130 upward away from the floor 74 of the raceway 70, thereby permitting the first roller arm 62 and the second roller arm 66 to move radially inward relative to the roller pump rotor 60 and/or away from the outer wall 72 (not shown) of the raceway 70. In some embodiments, the wedge 130 may comprise a uniform and/or symmetrical shape. In some embodiments, the wedge 130 may be generally conical so as to be able to engage with the first roller arm 62 and the second roller arm 66 in any rotational position around the central axis 61 of the roller pump rotor 60. Other configurations are also contemplated.

Figure 7:
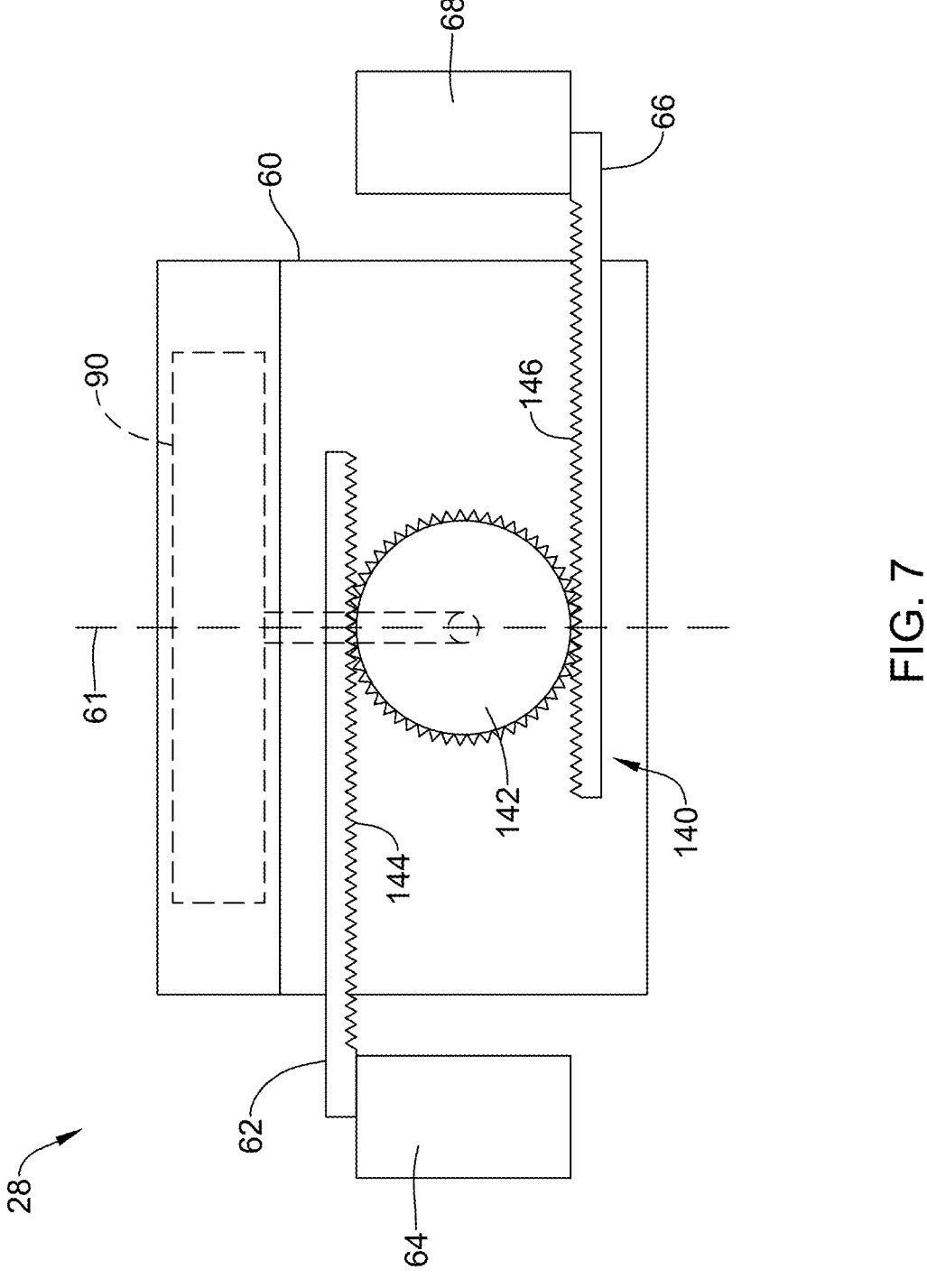
FIG. 7 schematically illustrates selected aspects of a roller pump in accordance with the disclosure.

FIG. 7 schematically illustrates selected aspects of another embodiment of the roller pump 28. In the interest of clarity, some features of the roller pump 28 are not shown. FIGS. 2-3 may be referred to for elements that are not expressly illustrated in FIG. 7. In some embodiments, the electronic actuator 90 may comprise and/or may be operatively coupled to a rack and pinion system 140 configured to change the radial position of the first roller 64 and the second roller 68 relative to the central axis 61 of the roller pump rotor 60. The rack and pinion system 140 may comprise a pinion gear 142 operatively coupled to the electronic actuator 90. The first roller arm 62 may comprise and/or may be fixedly secured to a first rack gear 144. The second roller arm 66 may comprise and/or may be fixedly secured to a second rack gear 146. The first rack gear 144 and the second rack gear 146 may be operatively engaged with the pinion gear 142 such that rotation of the pinion gear 142, by the electronic actuator 90 for example, causes the first rack gear 144 (and the first roller 64) and the second rack gear 146 (and the second roller 68) to move in opposite directions. When the pinion gear 142 rotates in a first direction, the first rack gear 144 (and the first roller 64) and the second rack gear 146 (and the second roller 68) may move radially outward relative to the roller pump rotor 60 and/or the central axis 61 of the roller pump rotor 60, and/or toward the outer wall 72 of the raceway 70 (e.g., FIGS. 2-3). When the pinion gear 142 rotates in a second direction opposite the first direction, the first rack gear 144 (and the first roller 64) and the second rack gear 146 (and the second roller 68) may move radially inward relative to the roller pump rotor 60 and/or the central axis 61 of the roller pump rotor 60, and/or away from the outer wall 72 of the raceway 70 (e.g., FIGS. 2-3). In some embodiments, the roller pump rotor 60 may comprise guides and/or supports for the first roller arm 62 and the second roller arm 66 to counteract cantilevered forces applied thereto by the first roller 64 and the second roller 68, respectively. Other configurations are also contemplated.

Figure 8:
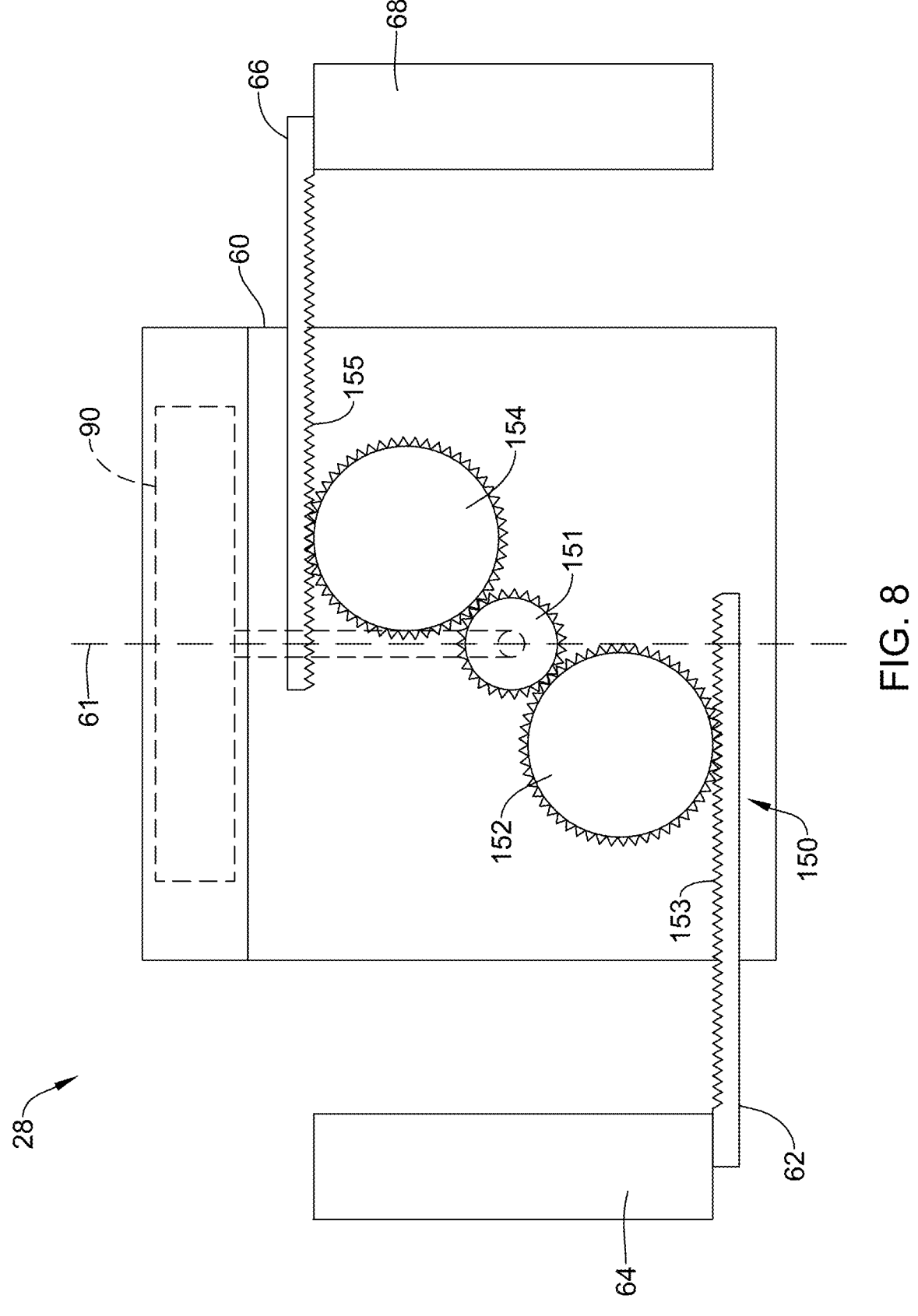
FIG. 8 schematically illustrates selected aspects of a roller pump in accordance with the disclosure.

FIG. 8 schematically illustrates selected aspects of another embodiment of the roller pump 28. In the interest of clarity, some features of the roller pump 28 are not shown. FIGS. 2-3 may be referred to for elements that are not expressly illustrated in FIG. 8. In some embodiments, the electronic actuator 90 may comprise and/or may be operatively coupled to a rack and pinion system 150 configured to change the radial position of the first roller 64 and the second roller 68 relative to the central axis 61 of the roller pump rotor 60. The rack and pinion system 150 may comprise a pinion gear 151 operatively coupled to the electronic actuator 90. The rack and pinion system 150 may comprise a first intermediate gear 152 operatively engaged with a first rack gear 153. The first roller arm 62 may comprise and/or may be fixedly secured to the first rack gear 153. The rack and pinion system 150 may comprise a second intermediate gear 154 operatively engaged with a second rack gear 155. The second roller arm 66 may comprise and/or may be fixedly secured to the second rack gear 155. Rotation of the pinion gear 151, by the electronic actuator 90 for example, causes the first rack gear 153 (and the first roller 64) and the second rack gear 155 (and the second roller 68) to move in opposite directions. When the pinion gear 151 rotates in a first direction, the first rack gear 153 (and the first roller 64) and the second rack gear 155 (and the second roller 68) may move radially outward relative to the roller pump rotor 60 and/or the central axis 61 of the roller pump rotor 60, and/or toward the outer wall 72 of the raceway 70 (e.g., FIGS. 2-3). When the pinion gear 151 rotates in a second direction opposite the first direction, the first rack gear 153 (and the first roller 64) and the second rack gear 155 (and the second roller 68) may move radially inward relative to the roller pump rotor 60 and/or the central axis 61 of the roller pump rotor 60, and/or away from the outer wall 72 of the raceway 70 (e.g., FIGS. 2-3). In some embodiments, the roller pump rotor 60 may comprise guides and/or supports for the first roller arm 62 and the second roller arm 66 to counteract cantilevered forces applied thereto by the first roller 64 and the second roller 68, respectively. Other configurations are also contemplated.

Figure 9:
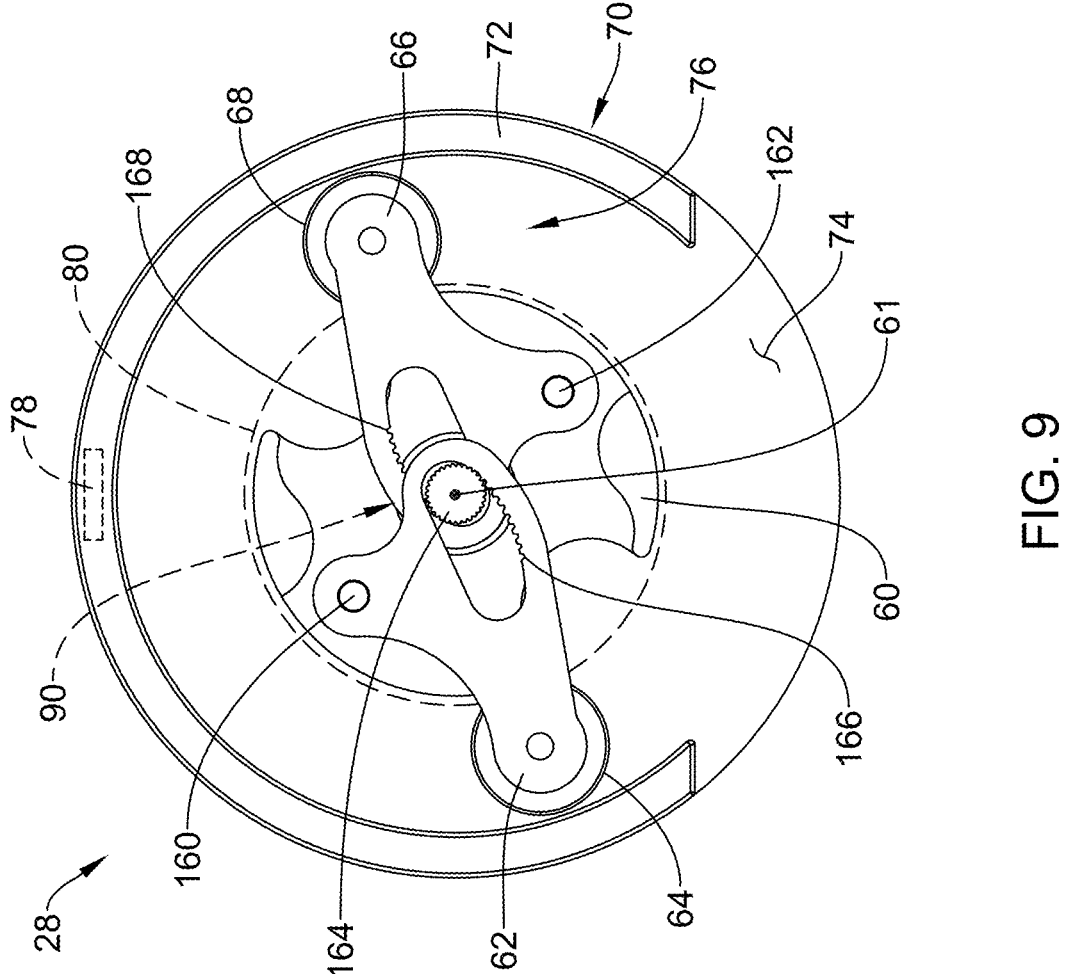
FIG. 9 schematically illustrates selected aspects of a roller pump in accordance with the disclosure.

FIG. 9 schematically illustrates selected aspects of another embodiment of the roller pump 28. Some features of the roller pump 28 may not be shown in the interest of clarity. At least some features of the roller pump 28 illustrated in FIG. 9 may be similar to and/or substantially the same as those shown in FIGS. 2-3. In the interest of brevity, disclosure related to those similar and/or same features is not duplicated herein.

The first roller arm 62 may be pivotably coupled to the roller pump rotor 60 at a first location 160. The second roller arm 66 may be pivotably coupled to the roller pump rotor 60 at a second location 162. In at least some embodiments, the second location 162 may be spaced part from the first location 160. The first roller arm 62 (and the first roller 64) and the second roller arm 66 (and the second roller 68) may be movable relative to the roller pump rotor 60 and/or a central axis 61 of the roller pump rotor 60. The first roller arm 62 (and the first roller 64) may be movable along a first arc relative to the roller pump rotor 60 and/or a central axis 61 of the roller pump rotor 60. The second roller arm 66 (and the second roller 68) may be movable along a second arc relative to the roller pump rotor 60 and/or a central axis 61 of the roller pump rotor 60. In some embodiments, a portion of the first roller arm 62 may overlap a portion of the second roller arm 66.

In some embodiments, the electronic actuator 90 may comprise a gear 164 disposed coaxial with the central axis 61 of the roller pump rotor 60. The gear 164 may be configured to engage the first roller arm 62 and the second roller arm 66 to change the radial position of the first roller 64 and the second roller 68 relative to the central axis 61 of the roller pump rotor 60 and/or relative to the outer wall 72 of the raceway 70. In some embodiments, the first roller arm 62 may comprise a first toothed cutout 166 formed therein, wherein the first toothed cutout 166 is configured to engage with the gear 164 to move the first roller arm 62 relative to the roller pump rotor 60. In some embodiments, the second roller arm 66 may comprise a second toothed cutout 168 formed therein, wherein the second toothed cutout 168 is configured to engage with the gear 164 to move the second roller arm 66 relative to the roller pump rotor 60. In at least some embodiments, the first toothed cutout 166 and the second toothed cutout 168 may surround the gear 164. In some embodiments, the first toothed cutout 166 and the second toothed cutout 168 may be configured to engage the gear 164 simultaneously.

Figure 10:
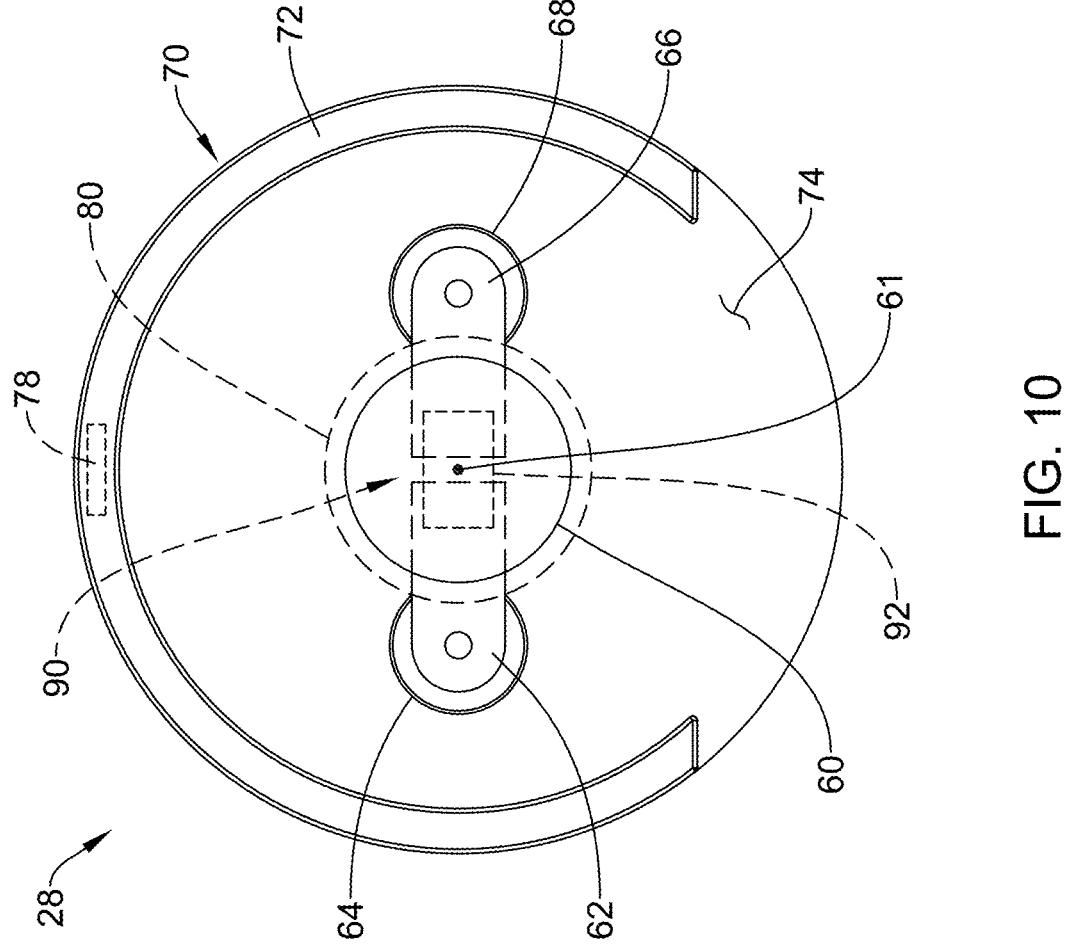
FIG. 10 schematically illustrates selected aspects of a roller pump in accordance with the disclosure.

FIG. 10 schematically illustrates selected aspects of another embodiment of the roller pump 28. Some features of the roller pump 28 may not be shown in the interest of clarity. At least some features of the roller pump 28 illustrated in FIG. 10 may be similar to and/or substantially the same as those shown in FIGS. 2-3. In the interest of brevity, disclosure related to those similar and/or same features is not duplicated herein.

In some embodiments, the electronic actuator 90 may be couplable to the pump motor 80 such that the pump motor 80 is capable of rotating the roller pump rotor 60 and changing the radial position of the first roller 64 and the second roller 68 relative to the roller pump rotor 60 and/or the central axis 61 of the roller pump rotor 60. In some embodiments, the electronic actuator 90 may comprise a clutch mechanism 92 configured to selectively couple the pump motor 80 with the first roller arm 62 and the second roller arm 66. The electronic actuator 90 may be configured to selectively actuate the clutch mechanism 92 when changing the radial position of the first roller 64 and the second roller 68 relative to the roller pump rotor 60 and/or the central axis 61 of the roller pump rotor 60 is desired. In some embodiments, the clutch mechanism 92 may be configured to couple the pump motor 80 with the first roller arm 62 and the second roller arm 66 while the pump motor 80 is running and/or while the first roller 64 and the second roller 68 are engaged with the flexible tubing 19. In some embodiments, the clutch mechanism 92 may be configured to engage with the pump motor 80, the first roller arm 62, and the second roller arm 66 simultaneously such that the pump motor 80 may be used to change the radial position of the first roller 64 and the second roller 68 relative to the roller pump rotor 60 and/or the central axis 61 of the roller pump rotor 60. Other configurations are also contemplated.

In some embodiments, a method of calibrating a roller pump 28 within an extracorporeal perfusion system 10 having a control unit 44 may comprise positioning the flexible tubing 19 within the raceway 70 of the roller pump 28, as seen in FIG. 3 for example. In some embodiments, the method of calibrating the roller pump 28 may comprise prior to positioning the flexible tubing 19 within the raceway 70 of the roller pump 28, priming the flexible tubing 19 with a fluid (e.g., blood, priming fluid, etc.). In some embodiments, priming the flexible tubing 19 may comprise supplying fluid (e.g., blood, priming fluid, etc.) into and/or through the flexible tubing 19 to remove air therefrom.

In some embodiments, the method of calibrating the roller pump 28 may comprise activating the roller pump 28 and/or the pump motor 80 to rotate the roller pump rotor 60, and/or the first roller arm 62 and the second roller arm 66, relative to the raceway 70 with the first roller 64 and the second roller 68 disposed in a radially innermost position (e.g., the parking position) corresponding to zero flow (e.g., a flow rate of zero) within the flexible tubing 19. In some embodiments, zero flow may include negligible flow wherein some flow rate greater than zero exists within the extracorporeal perfusion system 10 and/or the flexible tubing 19, but the roller pump 28 is not making any contribution to the flow rate.

In some embodiments, when activating the roller pump 28 and/or the pump motor 80 with the first roller 64 and the second roller 68 disposed in the radially innermost position (e.g., the parking position), the first roller 64 and the second roller 68 may be disengaged from the flexible tubing 19. In some embodiments, when activating the roller pump 28 and/or the pump motor 80 with the first roller 64 and the second roller 68 disposed in the radially innermost position (e.g., the parking position), the degree of occlusion of the flexible tubing 19 may be zero. When the degree of occlusion of the flexible tubing 19 is zero, no flow is generated within the flexible tubing 19 by the roller pump 28 (e.g., the flow rate of fluid within the flexible tubing 19 is zero or negligible, as discussed herein).

In some embodiments, the method of calibrating the roller pump 28 may comprise actuating and/or activating the electronic actuator 90, such as with the control unit 44, to change the radial position of the first roller 64 and the second roller 68 relative to the roller pump rotor 60 and/or the central axis 61 of the roller pump rotor 60. In some embodiments, the method of calibrating the roller pump 28 may comprise actuating and/or activating the electronic actuator 90, such as with the control unit 44, to move the first roller 64 and the second roller 68 radially outward from the radially inner most position (e.g., the parking position) until a flow rate greater than zero is measured within the extracorporeal perfusion system 10 and/or the flexible tubing 19, thereby indicating that the roller pump 28 is generating, contributing to, and/or adding to, the flow rate. In some embodiments, the first roller 64 and the second roller 68 may be moved radially outward from the radially inner most position (e.g., the parking position) slowly until a flow rate greater than zero is measured within the extracorporeal perfusion system 10 and/or the flexible tubing 19. In some embodiments, the first roller 64 and the second roller 68 may be configured to move radially outward from the radially inner most position (e.g., the parking position) at a fast speed (e.g., approximately 1 millimeter per second) until the first roller 64 and the second roller 68 make contact with an outer surface of the flexible tubing 19 and/or until a flow rate greater than zero is measured. In some embodiments, the first roller 64 and the second roller 68 may be configured to move radially outward from the radially inner most position (e.g., the parking position) at a slow speed (e.g., approximately 0.1 millimeter per second) to adjust the degree of occlusion of the flexible tubing 19 and/or the flow rate within the extracorporeal perfusion system 10 and/or the flexible tubing 19. Other speeds, speed ratios, and/or configurations are also contemplated.

In some embodiments, the method of calibrating the roller pump 28 may comprise storing a lower flow limit within the control unit 44, the lower flow limit corresponding to a first radially outermost position of the first roller 64 and the second roller 68 at which the flow rate within the extracorporeal perfusion system 10 and/or the flexible tubing 19 was measured at zero. In some embodiments, the lower flow limit may generally correspond to the radial position of the first roller 64 and the second roller 68 at which the first roller 64 and the second roller 68 first contact the flexible tubing 19 when moving the first roller 64 and the second roller 68 radially outward from the radially inner most position (e.g., the parking position).

In some embodiments, the method of calibrating the roller pump 28 may comprise, after storing the lower flow limit, actuating and/or activating the electronic actuator 90, such as via the control unit 44, to change the radial position of the first roller 64 and the second roller 68 relative to the roller pump rotor 60 and/or the central axis 61 of the roller pump rotor 60. In some embodiments, the method of calibrating the roller pump 28 may comprise, after storing the lower flow limit, actuating and/or activating the electronic actuator 90, such as with the control unit 44, to move the first roller 64 and the second roller 68 radially outward from the first radially outermost position of the first roller 64 and the second roller 68 until the flow rate measured within the extracorporeal perfusion system 10 and/or the flexible tubing 19 stops changing. As the first roller 64 and the second roller 68 move radially outward and the degree of occlusion of the flexible tubing 19 gradually increases, a maximum flow position of the first roller 64 and the second roller 68 will be reached at which no further increase in flow rate occurs (e.g., so-called full occlusion). In at least some embodiments, the maximum flow position and/or the upper flow limit occurs at and/or is achieved at less than full occlusion of the flexible tubing 19 (e.g., less than 100% occlusion, an occlusion gap greater than zero, etc.). Further occlusion of the flexible tubing 19 beyond the maximum flow position and/or the upper flow limit, such as reducing the occlusion gap to zero, may result in hemolysis (blood damage) in the flexible tubing 19, and/or may cause added and/or excessive stress to the flexible tubing 19, thereby shortening its useful life and/or increasing the potential for failure.

In some embodiments, the method of calibrating the roller pump 28 may comprise storing an upper flow limit within the control unit 44, the upper flow limit corresponding to a second radially outermost position of the first roller 64 and the second roller 68 at which the flow rate measured within the extracorporeal perfusion system 10 and/or the flexible tubing 19 stopped changing. The second radially outermost position of the first roller 64 and the second roller 68 may be disposed radially outward of the first radially outermost position of the first roller 64 and the second roller 68. The degree of occlusion of the flexible tubing 19 in the second radially outermost position of the first roller 64 and the second roller 68 is greater than the degree of occlusion of the flexible tubing 19 in the first radially outermost position of the first roller 64 and the second roller 68.

In some embodiments, the control unit 44 may comprise an automatic calibration mode configured to determine the lower flow limit within the flexible tubing 19 and the upper flow limit within the flexible tubing 19 without any further input from the user.

In some embodiments, the control unit 44 may be configured to automatically actuate and/or activate the electronic actuator 90 to set and/or to change the radial position of the first roller 64 and the second roller 68 based on a desired flow rate input into the control unit 44 by a user. In some embodiments, the control unit 44 may be configured to automatically actuate and/or activate the electronic actuator 90 to set and/or to change the radial position of the first roller 64 and the second roller 68 based on speed of the roller pump 28 and/or speed of the pump motor 80, and/the desired flow rate input into the control unit 44 by the user.

In some embodiments, the control unit 44 may be configured to automatically actuate and/or activate the electronic actuator 90 to set and/or to change the radial position of the first roller 64 and the second roller 68 to adjust the flow rate of fluid within extracorporeal perfusion system 10 and/or the flexible tubing 19. In some embodiments, the control unit 44 may be configured to automatically actuate and/or activate the electronic actuator 90 to set and/or to change the radial position of the first roller 64 and the second roller 68 to adjust the flow rate of fluid within extracorporeal perfusion system 10 and/or the flexible tubing 19 independently of speed of the roller pump 28 and/or speed of the pump motor 80. In some embodiments, the control unit 44 may be configured to automatically actuate and/or activate the electronic actuator 90 to set and/or to change the radial position of the first roller 64 and the second roller 68 to adjust the degree of occlusion of the flexible tubing 19 independently of speed of the roller pump 28 and/or speed of the pump motor 80.

In some embodiments, the control unit 44 may be configured to automatically actuate and/or activate the electronic actuator 90 to set, to adjust, and/or to change the radial position of the first roller 64 and the second roller 68 in response to pressure of fluid measured within the extracorporeal perfusion system 10 and/or the flexible tubing 19 by the pressure sensor 24.

In some embodiments, the control unit 44 may be configured to automatically actuate and/or activate the electronic actuator 90 to set, to adjust, and/or to change the radial position of the first roller 64 and the second roller 68 in response to force measured by the force sensor 78. In some embodiments, the control unit 44 may be configured to automatically actuate and/or activate the electronic actuator 90 to move the radial position of the first roller 64 and the second roller 68 radially outward if the force measured by the force sensor 78 decreases and no other parameters (such as flow rate and/or pressure of fluid, speed of the roller pump 28 and/or the pump motor 80, etc.) change. In some embodiments, a decrease in the force measured by the force sensor 78 combined with no other parameter changes may indicate the flexible tubing 19 is becoming worn, degraded, etc. In some embodiments, the control unit 44 may be configured to automatically actuate and/or activate the electronic actuator 90 to move the radial position of the first roller 64 and the second roller 68 radially inward if the force measured by the force sensor 78 increases and no other parameters (such as flow rate and/or pressure of fluid, speed of the roller pump 28 and/or the pump motor 80, etc.) change. In some embodiments, an increase in the force measured by the force sensor 78 combined with no other parameter changes may indicate the flexible tubing 19 is over compressed, over stressed, etc., which may lead to premature wear of the flexible tubing 19, excessive power consumption by the roller pump 28 and/or the pump motor 80, etc. In some embodiments, the control unit 44 may be configured to automatically actuate and/or activate the electronic actuator 90 to set, to adjust, and/or to change the radial position of the first roller 64 and the second roller 68 to compensate for physical changes in the flexible tubing 19 over time.

In some embodiments, the control unit 44 may be configured to automatically actuate and/or activate the electronic actuator 90 to set, to adjust, and/or to change the radial position of the first roller 64 and the second roller 68 to prevent backflow within the flexible tubing 19. For example, if the roller pump 28 and/or the pump motor 80 is shut down, the control unit 44 may be configured to automatically actuate and/or activate the electronic actuator 90 to change the radial position of the first roller 64 and the second roller 68 such that the flexible tubing 19 is fully occluded (e.g., the degree of occlusion is 100%), thereby preventing backflow within the flexible tubing 19. In some such embodiments, the roller pump 28 may be configured to act as and/or to replace the clamp 26 and/or multiple clamps, where present.

In some embodiments, the control unit 44 may be configured to automatically actuate and/or activate the electronic actuator 90 to set, to adjust, and/or to change the radial position of the first roller 64 and the second roller 68 to set an occlusion gap differential within the flexible tubing 19 based on user input into the control unit 44. In some embodiments, the user may wish to customize the occlusion gap within the flexible tubing 19. For example, in some procedures, the user may wish to set the occlusion gap to more or less than 100%, regardless of the impact or effect on flow rate, hemolysis, or other considerations.

In some embodiments, the control unit 44 may be configured to respond to user input during operation of the roller pump 28 and/or the pump motor 80 to automatically actuate and/or activate the electronic actuator 90 to set, to adjust, and/or to change the radial position of the first roller 64 and the second roller 68 based on the user input without deactivating or stopping the roller pump 28 and/or the pump motor 80. Other configurations are also contemplated.

In some embodiments, the control unit 44 may be configured to detect a size of the flexible tubing 19 by measuring hardness of the flexible tubing 19 with the force sensor 78 and comparing and/or correlating the hardness of the flexible tubing 19 measured with the force sensor 78 to a look-up table stored within the control unit 44. Other configurations are also contemplated.

The extracorporeal perfusion systems, roller pumps, and methods disclosed herein may advantageously permit automating setting the degree of occlusion of the roller pump and/or calibrating the roller pump. Such automation may improve ease of use for the attending personnel and may improve patient safety and procedural outcome because the process may be more repeatable and require less manual user intervention and/or less user-dependent set-up. Additionally, adjustment during the procedure or case based on blood parameters, etc. may be easier, safer, and/or improved.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is defined in the language in which the appended claims are expressed.

What is claimed is:

1. A roller pump, comprising:
a roller pump rotor comprising a first roller arm having a first roller rotatably coupled thereto and a second roller arm having a second roller rotatably coupled thereto;
a raceway disposed around the roller pump rotor and configured to receive a flexible tubing;
a pump motor configured to rotate the roller pump rotor relative to the raceway; and
an electronic actuator disposed on the roller pump rotor, wherein the electronic actuator is configured to change a radial position of the first roller relative to a central axis of the roller pump rotor and a radial position of the second roller relative to the central axis of the roller pump rotor;
wherein the first roller arm is pivotably coupled to the roller pump rotor at a first location and the second roller arm is pivotably coupled to the roller pump rotor at a second location spaced part from the first location;
wherein the electronic actuator comprises a gear disposed coaxial with the central axis of the roller pump rotor and the gear is configured to engage the first roller arm and the second roller arm to change the radial position of the first roller and the second roller relative to the central axis of the roller pump rotor.

2. The roller pump of claim 1, wherein the radial position of the first roller and the radial position of the second roller corresponds to a degree of occlusion of the flexible tubing.

3. The roller pump of claim 2, wherein as the radial position of the first roller and the radial position of the second roller moves away from the central axis of the roller pump rotor, the degree of occlusion of the flexible tubing increases.

4. The roller pump of claim 2, wherein as the radial position of the first roller and the radial position of the second roller moves toward the central axis of the roller pump rotor, the degree of occlusion of the flexible tubing decreases.

5. The roller pump of claim 1, wherein the electronic actuator functions independently of the pump motor to change the radial position of the first roller and the radial position of the second roller relative to the central axis of the roller pump rotor.

6. The roller pump of claim 5, wherein the electronic actuator is configured to change the radial position of the first roller and the radial position of the second roller relative to the central axis of the roller pump rotor while the pump motor is rotating the roller pump rotor relative to the raceway.

7. The roller pump of claim 1, wherein a portion of the first roller arm overlaps a portion of the second roller arm.

8. The roller pump of claim 1, wherein the raceway comprises a force sensor configured to sense force exerted against the flexible tubing by the first roller and the second roller.

9. The roller pump of claim 1, wherein the electronic actuator is configured to automatically change the radial position of the first roller and the radial position of the second roller relative to the roller pump rotor in order to maintain a desired flow rate through the flexible tubing.

10. The roller pump of claim 1, wherein the electronic actuator is configured to automatically change the radial position of the first roller and the radial position of the second roller relative to the roller pump rotor in response to pressure or flow rate of fluid within the flexible tubing.

11. An extracorporeal perfusion system, comprising:
a fluid reservoir;
an oxygenator;
flexible tubing fluidly coupling the fluid reservoir to the oxygenator; and
the roller pump of claim 1, wherein the flexible tubing is disposed within the raceway and the first roller and the second roller are engaged with the flexible tubing;
wherein the pump motor is configured to rotate the roller pump rotor relative to the raceway to cause fluid to flow within the flexible tubing from the fluid reservoir to the oxygenator.

12. A roller pump, comprising:
a roller pump rotor comprising a first roller arm having a first roller rotatably coupled thereto and a second roller arm having a second roller rotatably coupled thereto;
a raceway disposed around the roller pump rotor and configured to receive a flexible tubing;
a pump motor configured to rotate the roller pump rotor relative to the raceway; and
an electronic actuator disposed on the roller pump rotor, wherein the electronic actuator is configured to change a radial position of the first roller relative to a central axis of the roller pump rotor and a radial position of the second roller relative to the central axis of the roller pump rotor; and
a threaded mechanism configured to engage the first roller arm and the second roller arm such that actuation of the threaded mechanism by the electronic actuator changes the radial position of the first roller and the radial position of the second roller relative to the central axis of the roller pump rotor;

wherein the threaded mechanism comprises a threaded rod and a scissors assembly.

13. An extracorporeal perfusion system, comprising:

a fluid reservoir;

an oxygenator;

flexible tubing fluidly coupling the fluid reservoir to the oxygenator; and the roller pump of claim 12, wherein the flexible tubing is disposed within the raceway and the first roller and the second roller are engaged with the flexible tubing;

wherein the pump motor is configured to rotate the roller pump rotor relative to the raceway to cause fluid to flow within the flexible tubing from the fluid reservoir to the oxygenator.

14. A roller pump, comprising:

a roller pump rotor comprising a first roller arm having a first roller rotatably coupled thereto and a second roller arm having a second roller rotatably coupled thereto;

a raceway disposed around the roller pump rotor and configured to receive a flexible tubing;

a pump motor configured to rotate the roller pump rotor relative to the raceway; and an electronic actuator disposed on the roller pump rotor, wherein the electronic actuator is configured to change a radial position of the first roller relative to a central axis of the roller pump rotor and a radial position of the second roller relative to the central axis of the roller pump rotor; and a threaded mechanism configured to engage the first roller arm and the second roller arm such that actuation of the threaded mechanism by the electronic actuator changes the radial position of the first roller and the second roller relative to the central axis of the roller pump rotor;

wherein the threaded mechanism comprises:

a flattened disk having a center and a peripheral edge; and a spiral thread extending between the center and the peripheral edge;

wherein the first roller arm comprises threads configured to engage with the spiral thread of the threaded mechanism and the second roller arm comprises threads configured to engage with the spiral thread of the threaded mechanism.

15. An extracorporeal perfusion system, comprising:

a fluid reservoir;

an oxygenator;

flexible tubing fluidly coupling the fluid reservoir to the oxygenator; and the roller pump of claim 14, wherein the flexible tubing is disposed within the raceway and the first roller and the second roller are engaged with the flexible tubing;

wherein the pump motor is configured to rotate the roller pump rotor relative to the raceway to cause fluid to flow within the flexible tubing from the fluid reservoir to the oxygenator.

16. A roller pump, comprising:

a roller pump rotor comprising a first roller arm having a first roller rotatably coupled thereto and a second roller arm having a second roller rotatably coupled thereto;

a raceway disposed around the roller pump rotor and configured to receive a flexible tubing;

a pump motor configured to rotate the roller pump rotor relative to the raceway; and an electronic actuator disposed on the roller pump rotor, wherein the electronic actuator is configured to change a radial position of the first roller relative to a central axis of the roller pump rotor and a radial position of the second roller relative to the central axis of the roller pump rotor;

wherein the electronic actuator comprises a rack and pinion system configured to change the radial position of the first roller and the radial position of the second roller relative to the central axis of the roller pump rotor.

17. An extracorporeal perfusion system, comprising:

a fluid reservoir;

an oxygenator;

flexible tubing fluidly coupling the fluid reservoir to the oxygenator; and the roller pump of claim 16, wherein the flexible tubing is disposed within the raceway and the first roller and the second roller are engaged with the flexible tubing;

wherein the pump motor is configured to rotate the roller pump rotor relative to the raceway to cause fluid to flow within the flexible tubing from the fluid reservoir to the oxygenator.

18. A roller pump, comprising:

a roller pump rotor comprising a first roller arm having a first roller rotatably coupled thereto and a second roller arm having a second roller rotatably coupled thereto;

a raceway disposed around the roller pump rotor and configured to receive a flexible tubing;

a pump motor configured to rotate the roller pump rotor relative to the raceway; and an electronic actuator disposed on the roller pump rotor, wherein the electronic actuator is configured to change a radial position of the first roller relative to a central axis of the roller pump rotor and a radial position of the second roller relative to the central axis of the roller pump rotor;

wherein the electronic actuator is couplable to the pump motor such that the pump motor is capable of rotating the roller pump rotor and changing the radial position of the first roller and the radial position of the second roller relative to the roller pump rotor;

wherein the electronic actuator comprises a clutch mechanism configured to selectively couple the pump motor with the first roller arm and the second roller arm.

19. An extracorporeal perfusion system, comprising:

a fluid reservoir;

an oxygenator;

flexible tubing fluidly coupling the fluid reservoir to the oxygenator; and the roller pump of claim 18, wherein the flexible tubing is disposed within the raceway and the first roller and the second roller are engaged with the flexible tubing;

wherein the pump motor is configured to rotate the roller pump rotor relative to the raceway to cause fluid to flow within the flexible tubing from the fluid reservoir to the oxygenator.

* * * * *